(12) United States Patent
Haley et al.

US008377636B2

(10) Patent No.: US 8,377,636 B2
(45) Date of Patent: Feb. 19, 2013

(54) BIOLOGICAL MARKERS PREDICTIVE OF ANTI-CANCER RESPONSE TO KINASE INHIBITORS

(75) Inventors: John D. Haley, Sea Cliff, NY (US); Stuart Thompson, Port Washington, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 785 days.

(21) Appl. No.: 12/082,762

(22) Filed: Apr. 14, 2008

(65) Prior Publication Data

US 2008/0312260 A1 Dec. 18, 2008

Related U.S. Application Data

(60) Provisional application No. 60/923,463, filed on Apr. 13, 2007.

(51) Int. Cl.
*G01N 33/53* (2006.01)
*G01N 33/574* (2006.01)

(52) U.S. Cl. .............................. 435/4; 435/7.1; 435/7.23

(58) Field of Classification Search .................. None
See application file for complete search history.

(56) References Cited

U.S. PATENT DOCUMENTS

| | | | |
|---|---|---|---|
| 6,617,121 | B1 | 9/2003 | Garcia |
| 7,081,340 | B2 | 7/2006 | Baker |
| 2004/0106605 | A1 | 6/2004 | Carboni |
| 2004/0132097 | A1 | 7/2004 | Bacus |
| 2004/0209930 | A1 | 10/2004 | Carboni |
| 2005/0019785 | A1 | 1/2005 | Baker |
| 2006/0046249 | A1 | 3/2006 | Huang |
| 2006/0211060 | A1 | 9/2006 | Haley |
| 2007/0065858 | A1 | 3/2007 | Haley |
| 2007/0141621 | A1 | 6/2007 | Agus |
| 2007/0212738 | A1 | 9/2007 | Haley |
| 2007/0265185 | A1 | 11/2007 | Bouamrani |
| 2007/0270505 | A1 | 11/2007 | Bunn |
| 2008/0085519 | A1 | 4/2008 | Gabrin |
| 2008/0090233 | A1 | 4/2008 | Garcia |

FOREIGN PATENT DOCUMENTS

| | | |
|---|---|---|
| WO | 03078662 A1 | 9/2003 |
| WO | 2004046386 A1 | 6/2004 |
| WO | 2004063709 A2 | 7/2004 |
| WO | 2004065602 A1 | 8/2004 |
| WO | 2004071572 A2 | 8/2004 |
| WO | 2004111273 A2 | 12/2004 |
| WO | 2005017493 A2 | 2/2005 |
| WO | 2005067667 A2 | 7/2005 |
| WO | 2005070020 A2 | 8/2005 |
| WO | 2005094332 A2 | 10/2005 |
| WO | 2005099363 A2 | 10/2005 |
| WO | 2005107803 A2 | 11/2005 |
| WO | 2005117553 A2 | 12/2005 |
| WO | 2006099396 A2 | 9/2006 |
| WO | 2006101925 A2 | 9/2006 |
| WO | 2007028146 A2 | 3/2007 |
| WO | 2007035744 A1 | 3/2007 |
| WO | 2007075554 A2 | 7/2007 |
| WO | PCT/US2010/31144 | 4/2010 |

OTHER PUBLICATIONS

Thomson et al (Cancer Research, Oct. 15, 2005, 65:9455-9462).*
Croxtall et al (Biochimica et Biophysica Acta, 1998, 1401:39-51).*
Thomson et al (Clinical Exp. Metastasis, 2011, 28:137-155).*
Hammers et al (J Clinical Oncology, 2012, suppl 5; abstract 390).*
Thomson et al (Cancer Research, Oct. 15, 2005, 65:9455-9462, IDS).*
Hirsch, F.R. (2005) Curr. Opin. Oncol. 17:118-122.
Hoorens, A. et al. (May 1998) J. Pathol. 185(1): 53-60.
Huber, M. et al. (2005) Current Opinion in Cell Biology 17:548-558.
International Search Report of the International Search Authority in PCT/US2008/004819, 2008.
Written Opinion of the International Search Authority in PCT/US2008/004819, 2008.
Jain, A. et al. (2005) PNAS 102(33): 11858-11863.
Jaio, W. et al. (2002) British Journal of Cancer 86:98-101.
Janda, E. et al. (2002) J. Cell Biology 156(2):299-313.
Jawhari, A.U. et al (1999) J Pathol 187: 155-157.
Jechlinger, M. et al. (2006) The Journal of Clinical Investigation, http: www.jci.org, vol. 16(6): 1561-1570.
Jechlinger, M. et al. (2003) Oncogene 22: 7155-7169.
Kamalati, T. et al. (2000) Oncogene 19:5471-5476.
Kamalati, T. et al. (1996) J. Biol. Chemistry 271(48):30956-30963.
Kang, Y. et al. (2004) Cell 118(3):277-279.
Kassouf, W. et al. (2005) Cancer Res. 65(2):10524-10535.
Kiermer,A.K. et al. (2001) Oncogene 20:6679-6688.
Kim, K.S. et al. (2005) Clinical Cancer Research, 11:2244-2251.
Kobayashi, S. et al; (2005) New England Journal of Medicine 352:786-792.
Kokubo, Y. et al. (2005) British J. Cancer 92:1711-1719.
Kris, M.G. et al. JAMA 290(16):2149-2158 (2003).

(Continued)

*Primary Examiner* — Laura B Goddard
(74) *Attorney, Agent, or Firm* — Alexander A. Stewart; OSI Pharmaceuticals, LLC

(57) ABSTRACT

The present invention provides diagnostic and prognostic methods for predicting the effectiveness of treatment of a cancer patient with inhibitors of EGFR kinase, PDGFR kinase, or FGFR kinase. Based on the surprising discovery that tumors cells after having undergone an EMT, while being mesenchymal-like, still express characteristics of both epithelial and mesenchymal cells, and that such cells have altered sensitivity to inhibition by receptor protein-tyrosine kinase inhibitors, in that they have become relatively insensitive to EGFR kinase inhibitors, but have frequently acquired sensitivity to inhibitors of other receptor protein-tyrosine kinases such as PDGFR or FGFR, methods have been devised for determining levels of specific epithelial and mesenchymal biomarkers that identify such "hybrid" tumor cells (e.g. determination of co-expression of vimentin and epithelial keratins), and thus predict the tumor's likely sensitivity to inhibitors of EGFR kinase, PDGFR kinase, or FGFR kinase. Improved methods for treating cancer patients with EGFR, PDGFR or FGFR kinase inhibitors that incorporate such methodology are also provided.

9 Claims, 12 Drawing Sheets
(2 of 12 Drawing Sheet(s) Filed in Color)

OTHER PUBLICATIONS

Laasko, M. et al. (2006) Clinical Cancer Research: An official Journal of the American Association for Cancer Research 12: 14 part 1, 4185-4191.
Lan, M. et al. (2004) Carcinogenesis 25(12): 2385-2395.
Lee, J. M. et al. (2006) Journal of Cell Biology 172(7): 973-981.
Lemoine, N.R. et al. (1992) Br. J. Cancer 66:1116-11121.
Letters to Journal (2005) J of Clin. Onco. 23, No. 4, Feb. 1, 2005; pp. 923-924. (Downloaded from www.jco.org at OSI Pharmaceuticals on Feb. 28, 2006).
Lippman, S.M. et al. (2005) Clin. Cancer Res. 11(17):6097-6099.
Lu, Z. et al., (2003) Cancer Cell 4(6):499-515.
Markl, J. (1991) Journal of Cell Science 98: 261-264.
Matar, P. et al. (2004) Clin. Cancer Res. 10:6487-6501.
Matei, D. et al. (2006) Oncogene 25: 2060-2069.
Modern Pharmacology, 1990, Eds. Craig and Stitzel, Publishers, Little, Brown and Company, Chapter 60, pp. 776-778.
Moll, R. et al. (1982) Cell 31: 11-24.
Moody, S.E. (2005) Cancer Cell vol. 8, Sep. 2005, pp. 197-209.
Moon, H et al (2001) Gynecologic Oncology 81:355-359.
Ohira, T. et al. (2003) PNAS 100(18):10429-10434.
Oshima, RG (2002) Cell Death and Differentiation 9: 486-492.
Pece, S. et al. (275) J Biol Chem 275 (52): 41227-41233, (2000).
Perez-Soler, R. et al. (2003) Lung Cancer 41 (Suppl. 2), p. S72, Abstract O247.
Qian, X. et al (2004) EMBO 23:1739-1748.
Ramaekers, F.C.S. et al. (1987) Acta Histochemica Suppl. 34: 45-56.
Ramaekers, F.C.S. et al. (1983) Proc. Natl. Acad. Sci. USA 80: 2618-2622, May 1983, Cell Biology.
Sakurai, H. et al. (1997) Proc. Natl. Acad. Sci. USA, 94:6279-6284.
Sarrio, D et al. (2008) Cancer Research 68(4): 989-997.
Savagner, P. (2001) Bioessays 23:912-923.
Schaafsma, HE (May 1993) J. Pathol. 170(1): 77-86.
Schlessinger, K. et al. (2004) Nature Cell Biology 6(10):913-915.
Schussler,M.H. et al. (Mar. 1992) Am. J. Pathol. 140(3): 559-568.
Schrader, M. et al. (2007) Mol Cancer Ther 6(1): 277-285.
Shen, Xiaodong et al (2004) Amer J Path 165 (4): 1315-1329.
Struz, F. et al. (2002) Kidney International 61:1714-1728.
Sun, T.T. (1984) Cancer Cell 1, The Transformed Phonotype vol. 1; 169-176, Levine, A. et al. eds.; Cold Spring Harbor Laboratory.
Suto, et al. (1999) J. Can.Res.Clin. Oncol. 125:83-88.
Takenaka, K. et al. (2005) Cancer Epidemiology Biomarkers & Prevention 14(8):1972-1975.
Tejeda, M.L. et al. (2006) Clinical Cancer Research 2006:12(9): 2676-2688, May 1, 2006.
Thiery, J.P. (2002) Nat. Rev. Cancer 2:442-454.
Thomas, P.A. et al. (1999) Clinical Cancer Research 5: 2698-2703, Oct. 1999.
Thomson, S. et al. (2005) Cancer Res. 65(20):9455-9462.
Tuma, R.S. et al. (2005) J. Natl. Cancer Institute, 97(14):1028-1029.
Turley, E.A. et al. (2008) Nature Clinical Practice 5(5): 280-290.
Umemoto, et al. (2001) Brit. J. Can. 85:1032-1036.
Valdes, F. et al. (2002) Molecular Cancer Research, 1:68-78.
Valles, A. M. (1990) Proc. Natl. Acad. Sci. USA 87:1124-1128, Feb. 1990, Cell Biology.
Wilding, Jonathan et al. (1996) Cancer Res 56: 5285-5292.
Witta, S.E. et al. (2004) Proc. Amer. Assoc. Cancer Res. vol. 45 Abst. #3671, pp. 1-2.
Witta, S.E. et al. (2005) J. Clin. Oncol. vol. 23, No. 165 (Jun. 1 Suppl.) ASCO Proceedings Abst. #7083.
Witta, S.E. et al. (2006) Cancer Res. 66(2):944-950.
Xie, L. et al. (2004) Neoplasia 6(5): 603-610.
Yang, L. et al. (2006) Cell 127:139-155.
Yano, S. et al. (2003) Anticancer Res. 23 (5A): 3639-3650.
Yausch, R. L. et al. (2005) Clin. Cancer Res. 11:8686-8698.
Younes, M. (2005) J. Clinical Oncology 23(4): 923-924 (Downloaded from www.jco.org at OSI Pharmaceuticals on Feb. 28, 2006).
Zavadil, J. et al. (2005) Oncogene 24:5764-5774.
Richardson, F. et al. (2009) International Association for the Study of Lung Cancer, 13th World Conference on Lung Cancer, Jul. 31-Aug. 4, 2009, Moscone West, San Francisco, USA. "Comparison of E-cadherin IHC Status with Clinical Outcomes from Erlotinib in the Non Small Cell Lung Cancer (NSCLC) Clinical Trial NCIC CTG BR.21" e-Poster: PD72.5. Congress: WCLC 2009; 29 pages.
Sternberg, D., TAT Meeting, 8th International Symposium on Targeted Anticancer Therapies, Mar. 4-6, 2010. Bethesda, MD, USA, "The Development and Application of EMT Biomarkers in the Therapy of Solid Tumors"; 37 slides.
Nunes, M. et al (2004) Molecular Cancer Therapeutics 3(1): 21-27.
Aigner, K. et al. (2007) Oncogene pp. 1-10, Nature Publishing Group.
Amman, J. et al. (2005) Cancer Res. 65(1):226-235.
Andl, C. D., et al (2005) Cancer Biology and Therapy 4(1): 28-31.
Andl, C. D., et al (2003) J Biol Chem, 278 (No. 3):1824-1830.
Answers.com definition for "tumor", p. 1 (Apr. 17, 2009).
ATCC search Calu 6 (pp. 1-3; Mar. 10, 2010).
ATCC search H1703 (pp. 1-3; Mar. 10, 2010).
ATCC search H292 (pp. 1-3; Mar. 10, 2010).
ATCC search H358 (pp. 1-3; Mar. 10, 2010).
Auersberg, N. et al (1999) Proc Natl Acad Sci 96:6249-6254.
Babiychuk, E B et al. (2002) Bichimica et Biophysica Acta (BBA)—Proteins & Proteomics, Elsevier 1600, No. 1-2: 154-161.
Bailey et al. Proc. Am. Assoc. Res. 44:1362. abst. LB-170 (2003).
Bankfalvi, Agnes, et al (2002) J Oral Pathol Med 31: 450-457.
Barrallo-Gimeno, A. et al. (2005) Development 132:3151-3161.
Bates, R.C. et al. (2003) Current Biology 13.1721-1727.
Bergh, J. (1984) Expression of Intermediate Filaments in Established Human Lung Cancer Cell Lines. An indicator of Differentiation and Derivation Lab Invest 51(3): 307-316.
Bianco et al. (2005) Endocrine-related cancer 12:S159-S171.
Biowww.net; "BRK gene" definition; pp. 1-3; Mar. 9, 2010.
Brehmer, D. et al; (2005) Cancer Res. 65(2):379-382.
Broers, J.L.V. et al. (1988) Journal of Cell Science 83: 37-60.
Broers, J.L.V. et al. (1988) Journal of Cell Science 91: 91-108.
Buck, E. et al. (2007) Molecular Cancer Therapeutics 6(2): 532-541.
Buck, E. et al. (2006) Molecular Cancer Therapeutics 5(8): 2051-2059.
Camp, E.R. et al; (2005) Clinical Cancer Research (1):397-405.
Cano, A. et al; (2000) Nature Cell Biology 2: 76-83.
Castillo, L. et al. (2004) Annals of Oncology 15:1007-1012.
Chaffer, C. L. et al. (2006) Cancer Research 66(23): 11271-11278.
Chandler, L.A. (1999) Int. J. Cancer 82: 451-458.
Christofori, G. (2006) Nature 441(7092): 444-450.
Chung, L.W.K. et al. (2005) The Journal of Urology 173:10-20.
Ciruna, B. et al. (2001) Developmental Cell 1: 37-49.
Clara, B. et al. (2007) European Journal of Cancer Supplement 5:4, 366-367, abstract 6530.
Clark, D. M. et al. (1991) Histochemistry 96:5, 405-412.
Coltrera, M.D. (1995) Cancer Research 55: 2703-2708.
D'Souza, B. et al. (1994) Proc Natl Acad Sci 91:7202-7206.
Dai, Q. et al. (2005) Clinical Cancer Research 11:1572-1578.
Dancey, J. and Sausville, E.A. (2003) Nature Rev. Drug Discovery 2:296-313.
Dandachi, N. et al. (2001) J. Pathology; 193:181-189.
de Bono, J.S. and Rowinsky, E.K. (2002) Trends in Mol. Medicine 8(4): S19-S26.
De Craene, B. et al. (2005) Cancer Res. 65(14): 6237-6244.
Derwent / Delphion record for WO 2004065602, 2004.
Dumstrei, Karin et al (2002) Development 129: 3983-3994.
El-Deiry, W.S. (2005) Cancer Res. 65(11) :4475-4484.
Fedor-Chaiken, M. et al. (2003) Cell Communication and Adhesion 10:105-118.
Federick, B.A. et al. (2007) Mol Cancer Ther 6(6): 1683-1691.
Giaccone, G. (2005) Annals of Oncology 16: 538-548.
Grände, M. et al. (2202) J. Cell Science 115:4227-4236.
Grille, S.J. et al. (2003) Cancer Res. 63: 2172-2178.
Gura, T. (1997) Science 278: 1041-1042.
Hazan, R. B. et al. (1998) J Biol Chem 273 (15): 9078-9084.

* cited by examiner

B

C.

BIOLOGICAL MARKERS PREDICTIVE OF ANTI-CANCER RESPONSE TO KINASE INHIBITORS

CROSS-REFERENCE TO RELATED APPLICATIONS

This application claims the benefit of U.S. Provisional Application No. 60/923,463 filed Apr. 13, 2007, which is herein incorporated by reference in its entirety.

BACKGROUND OF THE INVENTION

The present invention is directed to methods for diagnosing and treating cancer patients. In particular, the present invention is directed to methods for determining which patients will most benefit from treatment with inhibitors of receptor protein-tyrosine kinases.

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide).

The epidermal growth factor receptor (EGFR) family comprises four closely related receptors (HER1/EGFR, HER2, HER3 and HER4) involved in cellular responses such as differentiation and proliferation. Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differentiation and increased tumor proliferation.

Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors, for example erlotinib (TARCEVA®) or gefitinib (IRESSA™), has been controversial. Recently, a mutant form of the full length EGF receptor has been reported to predict responsiveness to the EGF receptor tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of the EGF receptor (i.e. H3255) were more sensitive to growth inhibition by the EGF receptor tyrosine kinase inhibitor gefitinib, and that much higher concentrations of gefitinib was required to inhibit the tumor cell lines expressing wild type EGF receptor. These observations suggests that specific mutant forms of the EGF receptor may reflect a greater sensitivity to EGF receptor inhibitors, but do not identify a completely non-responsive phenotype.

The development for use as anti-tumor agents of compounds that directly inhibit the kinase activity of the EGFR, as well as antibodies that reduce EGFR kinase activity by blocking EGFR activation, are areas of intense research effort (de Bono J. S. and Rowinsky, E. K. (2002) Trends in Mol. Medicine. 8:S19-S26; Dancey, J. and Sausville, E. A. (2003) Nature Rev. Drug Discovery 2:92-313). Several studies have demonstrated, disclosed, or suggested that some EGFR kinase inhibitors might improve tumor cell or neoplasia killing when used in combination with certain other anti-cancer or chemotherapeutic agents or treatments (e.g. Herbst, R. S. et al. (2001) Expert Opin. Biol. Ther. 1:719-732; Solomon, B. et al (2003) Int. J. Radiat. Oncol. Biol. Phys. 55:713-723; Krishnan, S. et al. (2003) Frontiers in Bioscience 8, e1-13; Grunwald, V. and Hidalgo, M. (2003) J. Nat. Cancer Inst. 95:851-867; Seymour L. (2003) Current Opin. Investig. Drugs 4(6): 658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Ciardiello, F. et al. (2000) Clin. Cancer Res. 6:2053-2063; and Patent Publication No: US 2003/0157104).

Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in a number of human tumor cell lines, including colorectal and breast cancer (Moyer J. D. et al. (1997) Cancer Res. 57:4838), and preclinical evaluation has demonstrated activity against a number of EGFR-expressing human tumor xenografts (Pollack, V. A. et al (1999) J. Pharmacol. Exp. Ther. 291:739). More recently, erlotinib has demonstrated promising activity in phase I and II trials in a number of indications, including head and neck cancer (Soulieres, D., et al. (2004) J. Clin. Oncol. 22:77), NSCLC (Perez-Soler R, et al. (2001) Proc. Am. Soc. Clin. Oncol. 20:310a, abstract 1235), CRC (Oza, M., et al. (2003) Proc. Am. Soc. Clin. Oncol. 22:196a, abstract 785) and MBC (Winer, E., et al. (2002) Breast Cancer Res. Treat. 76:5115a, abstract 445). In a phase III trial, erlotinib monotherapy significantly prolonged survival, delayed disease progression and delayed worsening of lung cancer-related symptoms in patients with advanced, treatment-refractory NSCLC (Shepherd, F. et al. (2004) J. Clin. Oncology, 22:14S (July 15 Supplement), Abstract 7022). While most of the clinical trial data for erlotinib relate to its use in NSCLC, preliminary results from phase I/II studies have demonstrated promising activity for erlotinib and capecitabine/erlotinib combination therapy in patients with wide range of human solid tumor types, including CRC (Oza, M., et al. (2003) Proc. Am. Soc. Clin. Oncol. 22:196a, abstract 785) and MBC (Jones, R. J., et al. (2003) Proc. Am. Soc. Clin. Oncol. 22:45a, abstract 180). In November 2004 the U.S. Food and Drug Administration (FDA) approved TARCEVA® for the treatment of patients with locally advanced or metastatic non-small cell lung cancer (NSCLC) after failure of at least one prior chemotherapy regimen. TARCEVA® is the only drug in the epidermal growth factor receptor (EGFR) class to demonstrate in a Phase III clinical trial an increase in survival in advanced NSCLC patients.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well. Additionally, for any given cancer type one frequently cannot predict which patient is likely to respond to a particular treatment, even with newer gene-targeted therapies, such as EGFR kinase inhibitors, thus necessitating considerable trial and error, often at considerable risk and discomfort to the patient, in order to find the most effective therapy.

Thus, there is a need for more efficacious treatment for neoplasia and other proliferative disorders, and for more effective means for determining which tumors will respond to which treatment. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone).

Target-specific therapeutic approaches, such as erlotinib, are generally associated with reduced toxicity compared with conventional cytotoxic agents, and therefore lend themselves to use in combination regimens. Promising results have been observed in phase I/II studies of erlotinib in combination with bevacizumab (Mininberg, E. D., et al. (2003) Proc. Am. Soc. Clin. Oncol. 22:627a, abstract 2521) and gemcitabine (Dragovich, T., (2003) Proc. Am. Soc. Clin. Oncol. 22:223a, abstract 895). Recent data in NSCLC phase III trials have shown that first-line erlotinib or gefitinib in combination with standard chemotherapy did not improve survival (Gatzemeier, U., (2004) Proc. Am. Soc. Clin. Oncol. 23:617 (Abstract 7010); Herbst, R. S., (2004) Proc. Am. Soc. Clin. Oncol. 23:617 (Abstract 7011); Giaccone, G., et al. (2004) J. Clin. Oncol. 22:777; Herbst, R., et al. (2004) J. Clin. Oncol. 22:785). However, pancreatic cancer phase III trials have shown that first-line erlotinib in combination with gemcitabine did improve survival (OSI Pharmaceuticals/Genentech/Roche Pharmaceuticals Press Release, Sep. 20, 2004).

Several groups have investigated potential biomarkers to predict a patient's response to EGFR inhibitors (see for example, PCT publications: WO 2004/063709, WO 2005/017493, WO 2004/111273, WO 2004/071572, WO 2005/117553 and WO 2005/070020; and US published patent applications: US 2005/0019785, and US 2004/0132097). However, no diagnostic or prognostic tests have yet emerged that can guide practicing physicians in the treatment of their patients with EGFR kinase inhibitors.

The fibroblast growth factor signaling cascade consists of four transmembrane tyrosine kinase receptors (FGFR1-4) and at least 20 different ligands, providing a very complex and context dependent signaling axis. Signaling through this receptor activates a number of important regulators of cell survival and proliferation, including the MAP kinase and PI3K signaling pathways (Omtiz, D M. and Itoh, N. (2001) Genome Biol. 2: 3005). There is a large body of data to indicate that FGFR signaling plays a role in cancer development and progression. FGF receptors are overexpressed in a number of different cancer cell lines derived from a variety of different solid tumors (Chandler, L A., et al., (1999) Int. J. Cancer 81: 451). Functional inhibition of this pathway in these cell lines, by overexpression of dominant negative receptors (Aoki, T. et al., (2002) Int. J. Oncol. 21: 629) or by siRNA or antisense knockdown approaches (Estes Li, N R., et al., (2006) Oncol. Rep. 15: 1407; Yamada, S M., et al., 1999 Glia 28: 66), inhibited the growth and oncogenic potential of the tumor cells. Consistent with these in vitro observations, immunohistochemical staining of tumor tissue sections has indicated high expression of FGF receptors in breast (Wulfing, P., et al., (2005) Br. J. Cancer 92: 1720), prostate (Giri, D F., et al., (1999) Clin. Cancer Res. 5: 1063) and NSCLC (Volm, M R., et al., 1997 Eur. J. Cancer 33: 691) cancer patients. In addition, high FGFR1 expression was shown to be a predictor of poor survival in NSCLC (Volm, M R., et al., 1997 Eur. J. Cancer 33: 691) and pancreatic (Ohta, T., et al., (1995) Br. J. Cancer 72: 824) cancer patients. In further support of these observations Muller-Tudlow and colleagues observed that FGFR1 expression was one of the best predictors of poor survival in NSCLC when compared to a panel of 50 different receptor tyrosine kinases (Muller-Tidow, C., et al. (2005) Cancer Res. 65: 1778). These observations are consistent with the potential role of FGF receptors in more advanced metastatic cancer.

In this context it is interesting to point out that FGFR signaling has been implicated in epithelial to mesenchymal transition (EMT), a process by which cancer cells become more invasive and begin to metastasize. FGF signaling is a key regulator of SNAIL and E-cadherin levels in mouse development (Ciruna, B. and Rossant, J. (2001) Dev. Cell 1: 37) and has also been shown to induce EMT in tumor cells (Valles, A M, et al., (1990) PNAS 87: 1124). FGF-2, in conjunction with TGFβ, was shown to induce an EMT in tubular epithelial cells (Strutz, F., et al., (2002) Endocrinology 146:1145). Of most interest, a combination of FGF-2 and N-cadherin expression increased the metastatic potential of the normally weakly metatstatic breast cancer cell line MCF7 (Hazan, R B., et al., (2000) J. Cell Biol. 148: 779). Taken as a whole these results indicate that FGFR signaling plays a key role in the progression of cancer, potentially through its role in promoting EMT and, as a consequence, metatstasis of tumor cells.

The PDGF receptor signaling network consists of two receptors (PDGFRα and PDGFRβ), which can homo- or hetero-dimerize and 4 ligands (PDGF A-D), which also homo- or hetero-dimerise and differentially activate the different receptor dimers (Pietras, K., et al. (2003) Cancer Cell 3: 439). Ligand occupancy of these receptors results in the activation of a number of different intracellular signaling pathways including Ras and PI3K (Yu, J., et al. (2003) J. Biochem. Mol. Biol. 36: 49). Aberrant signaling by PDGFRs has been associated with cancer development and progression. Amplification of the PDGFRβ gene is associated with high-grade gliomas (Flemming, T P. et al. (1992) Cancer Res. 52: 4550) and gene-fusions involving the PDGFRβ gene have been reported in chronic myelomonocytic leukemia (CMML) (Golub, T R., et al. (1994) Cell 77: 307). Activating point mutations and deletions in the PDGFRα gene have also been reported in GIST patients (Heinrich, M C. et al., (2003) Science 299: 708). In addition increased autocrine PDGFR signaling, through increased expression of PDGF ligand, has been reported to be important in a number of glioma cell lines (Shamah, S M., et al. (1993) Mol. Cell. Biol. 13: 7203). Autocrine PDGFR has also been reported to be important in promoting progression and metastasis of tumors of epithelial origin such as ovarian (Matei, D., et al. (2006) Oncogene 25: 2060) and mammary cancer (Jechlinger, M., et al. (2006) J. Clin. Invest. 116: 1561).

Although these lines evidence support a role for the PDGF receptors in primary tumor biology, a key role for these receptors in cancer is in the regulation of the tumor microenviroment through paracrine signaling. PDGFRs are classically restricted to cells of a mesenchymal lineage and so are expressed in connective tissue fibroblasts. The expression of PDGF ligand from tumor cells acts as both a chemo attractant and a mitogen for PDGFR expressing stromal cells, leading to primary tumor development and promotion of angiogenesis. For example the growth of a NSCLC cell line Calu6, in a xenograft setting, was dependent upon tumor cell production of PDGF-AA allowing recruitment of mouse stromal cells to support primary tumor growth (Tejada, M L., et al. (2006) Human Cancer Biol. 12: 2676). Further, the potential importance of paracrine PDGFR signaling in advanced breast cancer was suggested by the observation that PDGF-BB ligand expression was restricted to tumor epithelial cells, whereas it was predominately the stromal cells adjacent to the tumor that expressed high levels of PDGF receptor (Coltrera et al., 1995). Therefore the paracrine signaling mediated by PDGFRs may be key in regulating the microenvironment to allow conditions supportive for primary tumor growth and the establishment of metastases at distant organ sites.

Another interesting, and related, aspect of PDGFR biology is that it has been implicated in EMT. Treatment of an epithelial colorectal cancer cell line, HT29, with PDGF induced all the hallmarks of a full EMT (Yang, L., et al. (2006) Cell 127: 139). In addition mouse epithelial cells stimulated with TGFβ show a marked increase in expression of PDGFRα, PDGFRβ and PDGF-AA. Signaling through this axis was crucial in maintaining the mesenchymal-like phenotype (Jechlinger, M., et al. (2006) J. Clin. Invest. 116: 1561). Taken together, these data indicate that PDGFR signaling either in an autocrine or paracrine fashion plays an important role in the development and progression of many different cancer types. These include the promotion of stromal cell recruitment and angiogenesis to provide a suitable tumor microenviroment and the stimulation and maintenance of EMT to promote tumor progression and metastasis.

During most cancer metastases, an important change occurs in a tumor cell known as the epithelial-mesenchymal transition (EMT) (Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515)). Epithelial cells, which are bound together tightly and exhibit polarity, give rise to mesenchymal cells, which are held together more loosely, exhibit a loss of polarity, and have the ability to travel. These mesenchymal cells can spread into tissues surrounding the original tumor, as well as separate from the tumor, invade blood and lymph vessels, and travel to new locations where they divide and form additional tumors. EMT does not occur in healthy cells except during embryogenesis. Under normal circumstances TGF-β acts as a growth inhibitor. However it is believed that during cancer metastasis, TGF-β begins to promote EMT.

Thus, there remains a critical need for improved methods for determining the best mode of treatment for any given cancer patient and for the incorporation of such determinations into more effective treatment regimens for cancer patients, whether such inhibitors are used as single agents or combined with other anti-cancer agents.

SUMMARY OF THE INVENTION

The present invention provides diagnostic and prognostic methods for predicting the effectiveness of treatment of a cancer patient with inhibitors of EGFR kinase, PDGFR kinase, or FGFR kinase. Based on the surprising discovery that tumors cells after having undergone an EMT, while being mesenchymal-like, still express characteristics of both epithelial and mesenchymal cells, and that such cells have altered sensitivity to inhibition by receptor protein-tyrosine kinase inhibitors, in that they have become relatively insensitive to EGFR kinase inhibitors, but have frequently acquired sensitivity to inhibitors of other receptor protein-tyrosine kinases such as PDGFR or FGFR, methods have been devised for determining levels of specific epithelial and mesenchymal biomarkers that identify such "hybrid" tumor cells, and thus predict the tumor's likely sensitivity to inhibitors of EGFR kinase, PDGFR kinase, or FGFR kinase.

Accordingly, the present invention provides a method of predicting the sensitivity of tumor cell growth to inhibition by an EGFR kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an EGFR kinase inhibitor, wherein co-expression of epithelial and mesenchymal biomarkers at similar levels correlates with (or is predictive of) low sensitivity to inhibition by EGFR kinase inhibitors, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

The present invention also provides a method of predicting the sensitivity of tumor cell growth to inhibition by a PDGFR or FGFR kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by a PDGFR or FGFR kinase inhibitor, wherein co-expression of epithelial and mesenchymal biomarkers at similar levels correlates with (or is predictive of) high sensitivity to inhibition by a PDGFR or FGFR kinase inhibitor, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

Improved methods for treating cancer patients with EGFR, PDGFR or FGFR kinase inhibitors that incorporate the above methodology are also provided. Thus, the present invention further provides a method for treating tumors or tumor metastases in a patient, comprising the steps of: diagnosing a patient's likely responsiveness to EGFR, PDGFR or FGFR kinase inhibitors by predicting the sensitivity of tumor cell growth to inhibition by EGFR, PDGFR or FGFR kinase inhibitors, comprising: assessing the level of an epithelial biomarker expressed by a tumor cell; assessing the level of a mesenchymal biomarker expressed by a tumor cell; and predicting the sensitivity of tumor cell growth to inhibition by EGFR, PDGFR or FGFR kinase inhibitors, wherein co-expression of epithelial and mesenchymal biomarkers at similar levels correlates with (or is predictive of) low sensitivity to inhibition by EGFR kinase inhibitors and high sensitivity to inhibition by PDGFR or FGFR kinase inhibitors, wherein the epithelial biomarker comprises one or more keratins selected from the epithelial keratins 1-28 and 71-80, and wherein the mesenchymal biomarker is vimentin, and administering to said patient a therapeutically effective amount of an EGFR kinase inhibitor if high sensitivity to inhibition by EGFR kinase inhibitors is predicted, or administering to said patient a therapeutically effective amount of a PDGFR or FGFR kinase inhibitor if low sensitivity to inhibition by EGFR kinase inhibitors is predicted. In one embodiment of this method one or more additional anti-cancer agents or treatments may be co-administered simultaneously or sequentially with the EGFR, PDGFR or FGFR kinase inhibitor. The additional anti-cancer agent or treatment may comprise an EGFR, PDGFR or FGFR kinase inhibitor, or any of the other cytotoxic, chemotherapeutic, antihormonal, anti-angiogenic, antiproliferative, pro-apoptotic, anti-HER2, radiation or a radiopharmaceutical, signal transduction inhibitors, or other anti-cancer agents or treatments listed herein. In one embodiment of the above methods the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

In a preferred embodiment of any of the above methods, the EGFR kinase inhibitor comprises erlotinib.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
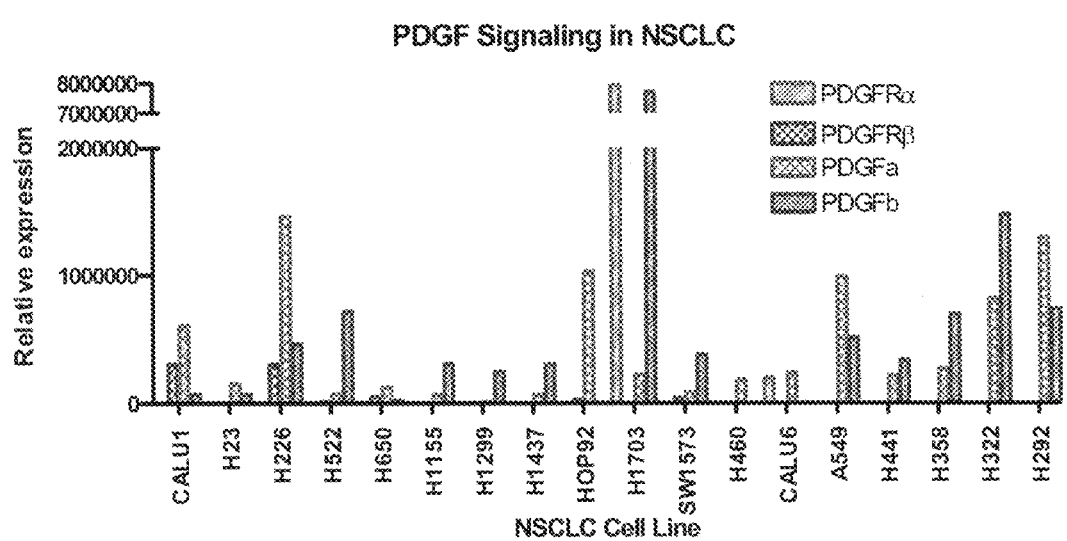
FIG. 1: Upregulation of PDGF Signaling Pathways in NSCLC. Total RNA was isolated from the indicated NSCLC cell lines. Expression levels of PDGFRα, PDGFRβ, PDGFα and PDGFb was determined by RT-PCR. The data was corrected to GAPDH expression in each cell line and plotted as relative expression (arbitary units).

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

As used herein, the term "platelet-derived growth factor" or "PDGF" refers to a member of a family of polypeptides that includes homo- or heterodimers of A-chain (PDGF-A) and B-chain (PDGF-B) that exert their action via binding to and dimerization of two related receptor tyrosine kinases, [α]-receptors (PDGFR-[α]) and [β]-receptors (PDGFR-[β]). It also includes PDGF-C and PDGF-D, two protease-activated ligands for the PDGFR complexes that also function as dimers (see Li et al., (2000) *Nat. Cell. Biol.* 2: 302-9; Bergsten et al., (2001) *Nat. Cell. Biol.* 3: 512-6; and Uutele et al., (2001) *Circulation* 103: 2242-47).

As used herein, the term "PDGF receptor" and "PDGFR" refers to cell surface PDGF-binding proteins. Two proteins that bind PDGF with high affinity have been identified, PDGFR-α and PDGFR-β (Heldin et al., (1981) *Proc. Natl. Acad. Sci.* (*USA*) 78: 3664; Williams et al., (1981) *Proc. Natl. Acad. Sci.* (*USA*) 79: 5867). Both species contain five immunoglobulin-like extracellular domains, a single transmembrane domain and an intracellular tyrosine kinase domain separated by a kinase insert domain, and can form homo- or hetero-dimers on binding PDGF. Due to the different ligand binding specificities of the PDGFRs it is known that PDGFR-[α][α] binds PDGF-AA, PDGF-BB, PDGF-AB, and PDGF-CC; PDGFR-[β][β] binds PDGF-BB and PDGF-DD; whereas PDGFR-[α][β] binds PDGF-AB, PDGF-BB, PDGF-CC, and PDGF-DD (see Betsholtz et al., (2001) *BioEssays* 23: 494-507).

As used herein, the term "fibroblast growth factor" or "FGF" refers to a member of a family of polypeptides that are potent regulators of a variety of cellular processes including proliferation, differentiation, migration, morphogenesis, tissue maintenance and in wound healing and repair (Clarke et al. (1993) J. Cell Sci. 106: 121-133; Cuevas et al. (1988) Biochem. Biophys. Res. Commun. 156: 611-618; Burgess, W. H. and Maciag, T (1989) Ann. Rev. Biochem. 58: 575-606; Rifkin, D. B. and Moscatelli, D. (1989) J. Cell Biol. 109:1-6). The FGF family currently includes at least 20 structurally and functionally related proteins, including acidic and basic FGF, FGF-1 and FGF-2 respectively; int2 (FGF-3); hst (FGF-4); FGF-5; hst2 (FGF-6); keratinocyte growth factor (FGF-7); androgen-induced growth factor (FGF-8); glia-activating factor (FGF-9); FGF-10-19 (Galzie, Z. et al. (1997) Biochem. Cell. Biol., 75:669-685; Yamasaki, M. et al. (1996) J. Biol. Chem., 271:15918-15921; Smallwood, P. M. et al. (1996) Proc. Natl. Acad. Sci. USA, 93:9850-9857; McWhirter, J. R. et al. (1997) Development, 124:3221-3232; Hoshikawa, M. et al. (1998) Biochem. Biophys. Res. Comm., 244:187-191; Hu, M. C. T. et al. (1998) Mol. Cell. Biol., 18:6063-6074; and Nishimura, T. et al. (1999) Biochim. Biophy. Acta, 1444:148-151). Preferably, the term FGF refers to acidic and basic FGF, FGF-1 and FGF-2, respectively (reviewed in (Galzie, Z. et al. (1997) Biochem. Cell. Biol., 75:669-685 and Burgess, W. H. and Maciag, T (1989) Ann. Rev. Biochem. 58: 575-606).

As used herein, the term "FGF receptor" and "FGFR" refers to FGF-binding polypeptides that possess intrinsic tyrosine kinase activity. There are currently four known genes encoding FGF receptors (FGFR-1, FGFR-2, FGFR-3, and FGFR-4), which can give rise to a variety of protein isoforms via alternative RNA splicing (Galzie, Z. et al. (1997) Biochem. Cell. Biol., 75:669-685). The structure of the FGFR consists of an extracellular region with three immunoglobulin-like domains, a transmembrane region, and a cytosolic tyrosine kinase domain that is activated upon ligand binding. FGF binding causes dimerization of the receptors, resulting in receptor autophosphorylation on tyrosine residues and the activation of intracellular signal transduction cascades.

The present invention provides diagnostic and prognostic methods for predicting the effectiveness of treatment of a cancer patient with inhibitors of EGFR kinase, PDGFR kinase, or FGFR kinase. The data presented in the Examples herein below demonstrate the surprising discovery that tumor cells, such as NSCLC cells, containing wild type EGFR, after having undergone an EMT, while being mesenchymal-like, still express characteristics of both epithelial and mesenchymal cells, and that such cells have altered sensitivity to inhibition by receptor protein-tyrosine kinase inhibitors, in that they have become relatively insensitive to EGFR kinase inhibitors, but have frequently acquired sensitivity to inhibitors of other receptor protein-tyrosine kinases such as PDGFR or FGFR. Methods have been devised for determining levels of specific epithelial and mesenchymal biomarkers that specifically identify such "hybrid" tumor cells, and thus predict the tumor's likely sensitivity to inhibitors of EGFR kinase, PDGFR kinase, or FGFR kinase.

Accordingly, the present invention provides a method of predicting the sensitivity of tumor cell growth to inhibition by an EGFR kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an EGFR kinase inhibitor, wherein co-expression of epithelial and mesenchymal biomarkers at similar levels correlates with (or is predictive of) low sensitivity to inhibition by EGFR kinase inhibitors, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

When used in any of the methods of the invention described herein, epithelial keratins 1-28 and 71-80 includes all the keratins listed in Table 1 herein.

The present invention also provides a method of predicting the sensitivity of tumor cell growth to inhibition by a PDGFR or FGFR kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by a PDGFR or FGFR kinase inhibitor, wherein co-expression of epithelial and mesenchymal biomarkers at similar levels correlates with (or is predictive of) high sensitivity to inhibition by a PDGFR or FGFR kinase inhibitor, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

The term "co-expression of epithelial and mesenchymal biomarkers at similar levels" as used herein means that the ratio of mesenchymal to epithelial biomarker levels is in the range of about 10:1 to about 1:10 (assuming that each biomarker is assayed under comparable conditions, e.g. using antibodies of identical affinity, nucleic acid probes of identical length, identical detection methods, etc.).

The term "a high ratio of mesenchymal to epithelial biomarkers" as used herein means that the ratio of mesenchymal to epithelial biomarker levels is greater than about 20:1 (assuming that each biomarker is assayed under comparable conditions, e.g. using antibodies of identical affinity, nucleic acid probes of identical length, identical detection methods, etc.).

Improved methods for treating cancer patients with EGFR, PDGFR or FGFR kinase inhibitors that incorporate the above methodology are also provided. Thus, the present invention further provides a method for treating tumors or tumor metastases in a patient, comprising the steps of: diagnosing a patient's likely responsiveness to EGFR, PDGFR or FGFR kinase inhibitors by predicting the sensitivity of tumor cell growth to inhibition by EGFR, PDGFR or FGFR kinase inhibitors, comprising: assessing the level of an epithelial biomarker expressed by a tumor cell; assessing the level of a mesenchymal biomarker expressed by a tumor cell; and predicting the sensitivity of tumor cell growth to inhibition by EGFR, PDGFR or FGFR kinase inhibitors, wherein co-expression of epithelial and mesenchymal biomarkers at similar levels correlates with (or is predictive of) low sensitivity to inhibition by EGFR kinase inhibitors and high sensitivity to inhibition by PDGFR or FGFR kinase inhibitors, wherein the epithelial biomarker comprises one or more keratins selected from the epithelial keratins 1-28 and 71-80, and wherein the mesenchymal biomarker is vimentin, and administering to said patient a therapeutically effective amount of an EGFR kinase inhibitor if high sensitivity to inhibition by EGFR kinase inhibitors is predicted, or administering to said patient a therapeutically effective amount of a PDGFR or FGFR kinase inhibitor if low sensitivity to inhibition by EGFR kinase inhibitors is predicted. In one embodiment of this method one or more additional anti-cancer agents or treatments may be co-administered simultaneously or sequentially with the EGFR, PDGFR or FGFR kinase inhibitor. The additional anti-cancer agent or treatment may comprise an EGFR, PDGFR or FGFR kinase inhibitor, or any of the other cytotoxic, chemotherapeutic, antihormonal, anti-angiogenic, antiproliferative, pro-apoptotic, anti-HER2, radiation or a radiopharmaceutical, signal transduction inhibitors, or other anti-cancer agents or treatments listed herein. In one embodiment of the above methods the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

In a preferred embodiment of any of the above methods, the EGFR kinase inhibitor comprises erlotinib.

One of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgement of the attending physician to determine the most appropriate course of treatment for an individual patient, based upon test results, patient condition and history, and his own experience. There may even be occasions, for example, when a physician will choose to treat a patient with an EGFR kinase inhibitor even when a tumor is not predicted to be particularly sensitive to EGFR kinase inhibitors, based on data from diagnostic tests or from other criteria, particularly if all or most of the other obvious treatment options have failed, or if some synergy is anticipated when given with another treatment. The fact that the EGFR kinase inhibitors as a class of drugs are relatively well tolerated compared to many other anti-cancer drugs, such as more traditional chemotherapy or cytotoxic agents used in the treatment of cancer, makes this a more viable option.

In the context of the methods of this invention, biomarkers expressed by a tumor cell can include molecular and cellular markers that indicate the "hybrid" transition state of the tumor cell. In a preferred embodiment the biomarker is an individual marker protein, or its encoding mRNA, characteristic of this particular transition state of the tumor cell, i.e. a tumor cell exhibiting epithelial and mesenchymal characteristics. In an alternative embodiment, in certain circumstances the biomarker may be a characteristic morphological pattern produced in the tumor cell by cellular macromolecules that is characteristic of the "hybrid" cell, mesenchymal-like condition.

TABLE 1

Molecular Biomarker Gene Identification

| Human Biomarker[3] | NCBI GeneID[1] | NCBI RefSeq[2] |
|---|---|---|
| Epithelial | | |
| keratin K1 | 3848 | NP_006112 |
| keratin K2 | 3849 | NP_000414 |
| keratin K3 | 3850 | NP_476429 |
| keratin K4 | 3851 | NP_002263 |

TABLE 1-continued

Molecular Biomarker Gene Identification

| Human Biomarker[3] | NCBI GeneID[1] | NCBI RefSeq[2] |
|---|---|---|
| keratin K5 | 3852 | NP_000415 |
| keratin K6a | 3853 | NP_005545 |
| keratin K6b | 3854 | NP_005546 |
| keratin K6c | 286887 | NP_775109 |
| keratin K7 | 3855 | NP_005547 |
| keratin K8 | 3856 | NP_002264 |
| keratin K9 | 3857 | NP_000217 |
| keratin K10 | 3858 | NP_000412 |
| keratin K12 | 3859 | NP_000214 |
| keratin K13 | 3860 | NP_002265 |
| keratin K14 | 3861 | NP_000517 |
| keratin K15 | 3866 | NP_002266 |
| keratin K16 | 3868 | NP_005548 |
| keratin K17 | 3872 | NP_000413 |
| keratin K18 | 3875 | NP_000215 |
| keratin K19 | 3880 | NP_002267 |
| keratin K20 | 54474 | NP_061883 |
| keratin K23 | 25984 | NP_056330 |
| keratin K24 | 192666 | NP_061889 |
| keratin K25 | 147183 | NP_853512 |
| keratin K26 | 353288 | NP_853517 |
| keratin K27 | 342574 | NP_853515 |
| keratin K28 | 162605 | NP_853513 |
| keratin K71 | 112802 | NP_258259 |
| keratin K72 | 140807 | NP_542785 |
| keratin K73 | 319101 | NP_778238 |
| keratin K74 | 121391 | NP_778223 |
| keratin K75 | 9119 | NP_004684 |
| keratin K76 | 51350 | NP_056932 |
| keratin K77 | 374454 | NP_778253 |
| keratin K78 | 196374 | NP_775487 |
| keratin K79 | 338785 | NP_787028 |
| keratin K80 | 144501 | NP_001074961 |
| Mesenchymal | | |
| vimentin | 7431 | NP_003371 |

[1]The NCBI GeneID number is a unique identifier of the biomarker gene from the NCBI Entrez Gene database record (National Center for Biotechnology Information (NCBI), U.S. National Library of Medicine, 8600 Rockville Pike, Building 38A, Bethesda, MD 20894; Internet address http://www.ncbi.nlm.nih.gov/).
[2]The NCBI RefSeq (Reference Sequence) is an example of a sequence expressed by the biomarker gene.
[3]The new consensus nomenclature has been used herein when referring to keratins (see Schweizer, J. et al. (2006) J. Cell Biol. 174(2): 169-174). Former names for these proteins can be found in the latter reference, and at the Human Intermediate Filament Database (http://www.interfil.org/index.php).

Table 1 lists the genes coding for examples of molecular biomarkers that can be used in the practice of the methods of the invention described herein. The molecular biomarkers can include any product expressed by these genes, including variants thereof, e.g. expressed mRNA or protein, splice variants, co- and post-translationally modified proteins, polymorphic variants etc. In an additional embodiment the biomarker can be an animal homologue of the human gene product (e.g. from dog, mouse, rat, rabbit, cat, monkey, ape, etc.). N.B. Epithelial keratins or cytokeratins are intermediate filament keratins. The terms "keratin" and "cytokeratin" are used synonymously herein. When referring to specific keratins in the text herein the "K" in the standard keratin designation (see Table 1) is generally dropped (e.g. keratin K8=keratin 8).

While co-expression of particular epithelial and mesenchymal biomarkers at similar levels is characteristic of mesenchymal-like "hybrid" tumor cells after EMT (e.g. keratins 8 and/or 18 and vimentin), certain other epithelial and mesenchymal biomarkers in hybrid tumor cells are expressed at levels more characteristic of either epithelial or mesenchymal cell types. Thus, assessment of the levels of these biomarkers in tumor cells from a patient can also be utilized for identifying mesenchymal-like tumor cells that may have high sensitivity to inhibition by a PDGFR or FGFR kinase inhibitor. The present invention thus also provides a method of predicting the sensitivity of tumor cell growth to inhibition by a PDGFR or FGFR kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by a PDGFR or FGFR kinase inhibitor, wherein a high ratio of mesenchymal to epithelial biomarkers correlates with (or is predictive of) high sensitivity to inhibition by a PDGFR or FGFR kinase inhibitor. In one embodiment of this method the epithelial biomarker is E-cadherin or γ-catenin, and the mesenchymal biomarker is fibronectin or vimentin. However, unlike the methods disclosed above for predicting the sensitivity of tumor cell growth to inhibition by a PDGFR or FGFR kinase inhibitor wherein co-expression of particular epithelial and mesenchymal biomarkers at similar levels correlates with (or is predictive of) high sensitivity to inhibition by a PDGFR or FGFR kinase inhibitor, this method may not unambiguously identify tumor cells with such sensitivities, since stromal cells may display a similar pattern of biomarker expression. Thus an additional evaluation of a test sample may be required to positively identify the cells as neoplastic or tumor cells.

Improved methods for treating cancer patients with PDGFR or FGFR kinase inhibitors that incorporate the above methodology are also provided. Thus, the present invention further provides a method for treating tumors or tumor metastases in a patient, comprising the steps of: diagnosing a patient's likely responsiveness to PDGFR or FGFR kinase inhibitors by predicting the sensitivity of tumor cell growth to inhibition by PDGFR or FGFR kinase inhibitors, comprising: assessing the level of an epithelial biomarker expressed by a tumor cell; assessing the level of a mesenchymal biomarker expressed by a tumor cell; predicting the sensitivity of tumor cell growth to inhibition by a PDGFR or FGFR kinase inhibitor, wherein a high ratio of mesenchymal to epithelial biomarkers correlates with (or is predictive of) high sensitivity to inhibition by a PDGFR or FGFR kinase inhibitor, and administering to said patient a therapeutically effective amount of a PDGFR or FGFR kinase inhibitor if high sensitivity to inhibition by a PDGFR or FGFR kinase inhibitor is predicted. In one embodiment of this method the epithelial biomarker is E-cadherin or γ-catenin, and the mesenchymal biomarker is fibronectin or vimentin. In one embodiment of this method one or more additional anti-cancer agents or treatments may be co-administered simultaneously or sequentially with the PDGFR or FGFR kinase inhibitor. The additional anti-cancer agent or treatment may comprise an EGFR, PDGFR or FGFR kinase inhibitor, or any of the other cytotoxic, chemotherapeutic, antihormonal, anti-angiogenic, antiproliferative, pro-apoptotic, anti-HER2, radiation or a radiopharmaceutical, signal transduction inhibitors, or other anti-cancer agents or treatments listed herein.

Examples of epithelial markers that can be used in the method above for predicting the sensitivity of tumor cell growth to inhibition by a PDGFR or FGFR kinase inhibitor, wherein a high ratio of mesenchymal to epithelial biomarkers correlates with (or is predictive of) high sensitivity to inhibition by a PDGFR or FGFR kinase inhibitor, include E-cadherin, Brk, γ-catenin, α1-catenin, α2-catenin, α3-catenin, connexin 31, plakophilin 3, stratafin 1, laminin alpha-5, ST 14, phospho-14-3-3 epsilon, 14-3-3 gamma (KCIP-1), 14-3-3 sigma (Stratifin), 14-3-3 zeta/delta, phospho-serine/threonine phosphatase 2A, 4F2hc (CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER)., Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Casein kinase I, alpha, Protein kinase C, delta, Pyruvate kinase, isozymes M1/M2, phospho-Erbin, LIM and SH3 domain protein 1 (LASP-1), 4F21c (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, and phospho-SHC1. Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

Examples of mesenchymal markers that can be used in the method above for predicting the sensitivity of tumor cell growth to inhibition by a PDGFR or FGFR kinase inhibitor, wherein a high ratio of mesenchymal to epithelial biomarkers correlates with (or is predictive of) high sensitivity to inhibition by a PDGFR or FGFR kinase inhibitor, include vimentin, fibronectin, fibrillin-1, fibrillin-2, collagen alpha-2(IV), collagen alpha-2(V), LOXL1, nidogen, C11orf9, tenascin, N-cadherin, embryonal EDB+ fibronectin, tubulin alpha-3, epimorphin, MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1,3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-H1stone H2AFX, phospho-H1stone H2A.o, phospho-H1stone H2A.q, phospho-H1stone H2A.z, phospho-Histone H2Bj, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent PK1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, and SHC1. Where the mesenchymal biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

The above lists of epithelial and mesenchymal biomarkers have been identified as being altered in expression level (or phosphoylation level for phospho-"proteins") after EMT (see for example, the US application which is a continuation-in-part of U.S. application Ser. No. 11/377,530 (filed Mar. 16, 2006), which was filed on the same day as the instant application, and the contents of which are incorporated herein by reference; US Published Application 2006/0211060 (filed Mar. 16, 2006); Thomson, S. et al. (2005) Cancer Res. 65(20) 9455-9462; and Yauch, R. L. et al. (2005) Clin. Can. Res. 11(24) 8686-8698).

In the methods described herein the tumor cell will typically be from a patient diagnosed with cancer, a precancerous condition, or another form of abnormal cell growth, and in need of treatment. The cancer may be lung cancer (e.g. non-small cell lung cancer (NSCLC)), pancreatic cancer, head and neck cancer, gastric cancer, breast cancer, colon cancer, ovarian cancer, or any of a variety of other cancers described herein below. The cancer is preferably one known to be potentially treatable with an EGFR kinase inhibitor.

In the methods of this invention, biomarker expression level can be assessed relative to a control molecule whose expression level remains constant throughout EMT, or when comparing tumor cells expressing either epithelial or mesenchymal transition states as indicated by molecular biomarkers (e.g. a "housekeeping" gene, such as GAPDH, β-actin, tubulin, or the like). Biomarker expression level can also be assessed relative to the other type of tumor cell biomarker (i.e. epithelial compared to mesenchymal), or to the biomarker level in non-tumor cells of the same tissue, or another cell or tissue source used as an assay reference.

In the methods of this invention, the level of an epithelial or mesenchymal biomarker expressed by a tumor cell can be assessed by using any of the standard bioassay procedures known in the art for determination of the level of expression of a gene, including for example ELISA, RIA, immunoprecipitation, immunoblotting, immunofluorescence microscopy, immunohistochemistry (IHC), RT-PCR, in situ hybridization, cDNA microarray, or the like, as described in more detail below. In an embodiment of any of these methods, their use is coupled with a method to isolate a particular cell population, e.g. laser capture microdissection (LCM).

In the methods of this invention, the expression level of a tumor cell epithelial or mesenchymal biomarker is preferably assessed by assaying a tumor biopsy. In one embodiment the biopsy comprises samples taken from multiple areas of the tumor, or a method (e.g. core needle biopsy) that samples different areas of the tumor, thus ensuring that when the tumor is of a heterogeneous nature with respect to the types of cells it contains, that a representative biopsy is obtained. In a preferred embodiment, when the tumor is heterogeneous with respect to the types of cells it contains, the diagnostic methods of the invention described herein for predicting tumor sensitivity to inhibitors are preferably applied separately to different cell types (e.g. using IHC, or an analysis method coupled with a step to isolate a particular cell population). However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor epithelial or mesenchymal biomarkers in such bodily fluids or excretions can sometimes be preferred in circumstances where an invasive sampling method is inappropriate or inconvenient.

In the methods of this invention, the tumor cell can be a lung cancer tumor cell (e.g. non-small cell lung cancer (NSCLC)), a pancreatic cancer tumor cell, a breast cancer tumor cell, a head and neck cancer tumor cell, a gastric cancer tumor cell, a colon cancer tumor cell, an ovarian cancer tumor cell, or a tumor cell from any of a variety of other cancers as described herein below. The tumor cell is preferably of a type known to or expected to express EGFR kinase, as do all tumor cells from solid tumors. The EGFR kinase can be wild type or a mutant form.

In the methods of this invention, the EGFR kinase inhibitor can be any EGFR kinase inhibitor as described herein below, but is preferably 6,7-bis(2-methoxyethoxy)-4-quinazolin-4-yl]-(3-ethynylphenyl) amine (also known as erlotinib, OSI-774, or TARCEVA® (erlotinib HCl), including pharmacologically acceptable salts or polymorphs thereof.

The following methods represent additional specific embodiments of the method of the invention.

The present invention provides a method of predicting the sensitivity of tumor growth to inhibition by an EGFR kinase inhibitor, comprising: assessing the level of an epithelial biomarker expressed by cells of the tumor; assessing the level of a mesenchymal biomarker expressed by cells of the tumor; and predicting the sensitivity of tumor growth to inhibition by an EGFR kinase inhibitor, wherein co-expression of epithelial and mesenchymal biomarkers at similar levels correlates with (or is predictive of) low sensitivity to inhibition by EGFR kinase inhibitors, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

The present invention also provides a method of predicting the sensitivity of tumor growth to inhibition by a PDGFR or FGFR kinase inhibitor, comprising: assessing the level of an epithelial biomarker expressed by cells of the tumor; assessing the level of a mesenchymal biomarker expressed by cells of the tumor; and predicting the sensitivity of tumor growth to inhibition by a PDGFR or FGFR kinase inhibitor, wherein co-expression of epithelial and mesenchymal biomarkers at similar levels correlates with (or is predictive of) high sensitivity to inhibition by a PDGFR or FGFR kinase inhibitor, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

The present invention provides a method of predicting whether a cancer patient is afflicted with a tumor that will respond effectively to treatment with an EGFR kinase inhibitor, comprising: assessing the level of an epithelial biomarker expressed by cells of the tumor; assessing the level of a mesenchymal biomarker expressed by cells of the tumor; and predicting if the tumor will respond effectively to treatment with an EGFR kinase inhibitor, wherein co-expression of epithelial and mesenchymal biomarkers at similar levels correlates with (or is predictive of) a tumor that may not respond effectively to treatment with an EGFR kinase inhibitor, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

The present invention provides a method of predicting whether a cancer patient is afflicted with a tumor that will respond effectively to treatment with a PDGFR or FGFR kinase inhibitor, comprising: assessing the level of an epithelial biomarker expressed by cells of the tumor; assessing the level of a mesenchymal biomarker expressed by cells of the tumor; and predicting if the tumor will respond effectively to treatment with a PDGFR or FGFR kinase inhibitor, wherein co-expression of epithelial and mesenchymal biomarkers at similar levels correlates with (or is predictive of) a tumor that may respond effectively to treatment with a PDGFR or FGFR kinase inhibitor, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

In any of the methods of this invention, the tumor can be a lung cancer tumor (e.g. non-small cell lung cancer (NSCLC)), a pancreatic cancer tumor, a breast cancer tumor, a head and neck cancer tumor, a gastric cancer tumor, a colon cancer tumor, an ovarian cancer tumor, or a tumor from any of a variety of other cancers as described herein below. The tumor is preferably of a type whose cells are known to or expected to express EGFR kinase, as do all solid tumors. The EGFR kinase can be wild type or a mutant form.

The present invention provides a method of determining the likelihood that a patient with a tumor will gain survival benefit from therapy with an EGFR kinase inhibitor, comprising: assessing the level of an epithelial biomarker expressed by cells of the tumor; assessing the level of a mesenchymal biomarker expressed by cells of the tumor; and predicting if the tumor will respond effectively to treatment with an EGFR kinase inhibitor, wherein co-expression of epithelial and mesenchymal biomarkers at similar levels correlates with (or is predictive of) a tumor that may not respond effectively to treatment with an EGFR kinase inhibitor, and thus being indicative that the patient may not gain significant survival benefit from therapy with an EGFR kinase inhibitor, wherein the epithelial biomarker comprises one or more keratins selected from the epithelial keratins 1-28 and 71-80, and wherein the mesenchymal biomarker is vimentin. In one embodiment the epithelial keratin(s) are assessed using a method that will detect all or the majority (i.e. 50% or more) of the keratin biomarkers expressed by the tumor cell (e.g. by using a multi- or pan-specific antibody). In another embodiment the epithelial biomarker comprises keratin 8 and/or keratin 18.

For assessment of tumor cell epithelial or mesenchymal biomarker expression, patient samples containing tumor cells, or proteins or nucleic acids produced by these tumor cells, may be used in the methods of the present invention. In these embodiments, the level of expression of the biomarker can be assessed by assessing the amount (e.g. absolute amount or concentration) of the marker in a tumor cell sample, e.g., a tumor biopsy obtained from a patient, or other patient sample containing material derived from the tumor (e.g. blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies may also be subjected to post-collection preparative and storage techniques, e.g., fixation.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from cells in a patient sample, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s). Alternatively, any of the many known methods of detecting mutations or variants (e.g. single nucleotide polymorphisms, deletions, etc.) of a biomarker of the invention may be used to detect occurrence of a biomarker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type, either in a single reaction mixture (i.e. using reagents, such as different fluorescent probes, for each biomarker) or in individual reaction mixtures corresponding to one or more of the biomarkers.

The level of expression of a biomarker in normal (i.e. non-cancerous) human tissue can be assessed in a variety of ways. In one embodiment, this normal level of expression is assessed by assessing the level of expression of the biomarker in a portion of cells which appears to be non-cancerous, and then comparing this normal level of expression with the level of expression in a portion of the tumor cells. Alternately, and particularly as further information becomes available as a result of routine performance of the methods described herein, population-average values for normal expression of the biomarkers of the invention may be used. In other embodiments, the 'normal' level of expression of a biomarker may be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g. a tumor-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second acceptor molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S, and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; Hage, D. S., and Tweed, S. A. J. Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g. a mesenchymal biomarker), the level of expression of the biomarker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. A preferred agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reductive methylation for $^{3}H$. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

The invention also encompasses kits for detecting the presence of a biomarker protein or nucleic acid in a biological sample. Such kits can be used to determine if a subject is suffering from or is at increased risk of developing a tumor that is less susceptible to inhibition by EGFR kinase inhibitors. For example, the kit can comprise a labeled compound or agent capable of detecting a biomarker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a biomarker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

It will be appreciated by one of skill in the medical arts that the exact manner of administering to said patient of a therapeutically effective amount of an EGFR kinase inhibitor following a diagnosis of a patient's likely responsiveness to an EGFR kinase inhibitor will be at the discretion of the attending physician. The mode of administration, including dosage, combination with other anti-cancer agents, timing and frequency of administration, and the like, may be affected by the diagnosis of a patient's likely responsiveness to an EGFR kinase inhibitor, as well as the patient's condition and history. Thus, even patients diagnosed with tumors predicted to be relatively insensitive to EGFR kinase inhibitors may still benefit from treatment with such inhibitors, particularly in combination with other anti-cancer agents, or agents that may alter a tumor's sensitivity to EGFR kinase inhibitors.

The effectiveness of treatment in the preceding methods can for example be determined by measuring the decrease in size of tumors present in the patients with the neoplastic condition, or by assaying a molecular determinant of the degree of proliferation of the tumor cells.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, one or more other cytotoxic, chemotherapeutic or anti-cancer agents, or compounds that enhance the effects of such agents.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4,20-nitro-3-(trifluoromethyl) phenylpropanamide), commercially available as EULEXIN® (Schering Corp.); the non-steroidal anti-androgen nilutamide, (5,5-dim-ethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 4,1530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/ urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606, 046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, one or more tumor cell pro-apoptotic or apoptosis-stimulating agents.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors (e.g. BAY 43-9006, Onyx Pharmaceuticals/Bayer Pharmaceuticals); MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, an anti-HER2 antibody or an immunotherapeutically active fragment thereof.

The present invention further provides the preceding methods for treating tumors or tumor metastases in a patient, comprising administering to the patient a therapeutically effective amount of an EGFR kinase inhibitor and in addition, simultaneously or sequentially, one or more additional antiproliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217.

The present invention further provides the preceding methods for treating tumors or tumor metastases in a patient, comprising administering to the patient a therapeutically effective amount of an EGFR kinase inhibitor and in addition, simultaneously or sequentially, a COX II (cyclooxygenase II) inhibitor. Examples of useful COX-II inhibitors include alecoxib (e.g. CELEBREX™), valdecoxib, and rofecoxib.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the inhibitor of EGFR kinase, FGFR kinase, or PDGFR kinase, according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides the preceding methods for treating tumors or tumor metastases in a patient, comprising administering to the patient a therapeutically effective amount of an inhibitor of EGFR kinase, FGFR kinase, or PDGFR kinase, and in addition, simultaneously or sequentially, treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

As used herein, the term "patient" preferably refers to a human in need of treatment with an EGFR kinase inhibitor for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an EGFR kinase inhibitor.

In a preferred embodiment, the patient is a human in need of treatment for cancer, a precancerous condition or lesion, or other forms of abnormal cell growth. The cancer is preferably any cancer treatable, either partially or completely, by administration of an EGFR kinase inhibitor. The cancer may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

For purposes of the present invention, "co-administration of" and "co-administering" an inhibitor of EGFR kinase, FGFR kinase, or PDGFR kinase, with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the inhibitor of EGFR kinase, FGFR kinase, or PDGFR kinase, or in some combination thereof. Where the inhibitor of EGFR kinase, FGFR kinase, or PDGFR kinase, is administered to the patient at repeated intervals, e.g., during a standard course of treatment, the additional agent can be administered prior to, at the same time as, or subsequent to, each administration of the inhibitor of EGFR kinase, FGFR kinase, or PDGFR kinase, or some combination thereof of these modes, or at different intervals in relation to the treatment with the inhibitor of EGFR kinase, FGFR kinase, or PDGFR kinase, or in a single dose prior to, at any time during, or subsequent to the course of treatment with the inhibitor of EGFR kinase, FGFR kinase, or PDGFR kinase.

The inhibitor of EGFR kinase, FGFR kinase, or PDGFR kinase, will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574 (others for PDGFR, FGFR). In conducting the treatment method of the present invention, the inhibitor of EGFR kinase, FGFR kinase, or PDGFR kinase, can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of kinase inhibitor being used (for example, small molecule, antibody, RNAi, ribozyme or antisense construct), and the medical judgement of the prescribing physician as based, e.g., on the results of published clinical studies.

The amount of inhibitor of EGFR kinase, FGFR kinase, or PDGFR kinase administered and the timing of kinase inhibitor administration will depend on the type (species, gender, age, weight, etc.) and condition of the patient being treated, the severity of the disease or condition being treated, and on the route of administration. For example, small molecule kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The inhibitor of EGFR kinase, FGFR kinase, or PDGFR kinase, and other additional agents can be administered either separately or together by the same or different routes, and in a wide variety of different dosage forms. For example, the kinase inhibitor is preferably administered orally or parenterally. Where the EGFR kinase inhibitor is erlotinib HCl (TARCEVA®), oral administration is preferable. Both the inhibitor of EGFR kinase, FGFR kinase, or PDGFR kinase, and other additional agents can be administered in single or multiple doses.

The inhibitor of EGFR kinase, FGFR kinase, or PDGFR kinase can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The inhibitor of EGFR kinase, FGFR kinase, or PDGFR kinase can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous inhibitors of EGFR kinase, FGFR kinase, or PDGFR kinase, should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. In view of the teaching of the present invention, methods of preparing pharmaceutical compositions comprising an inhibitor of EGFR kinase, FGFR kinase, or PDGFR kinase, will be apparent from the above-cited publications and from other known references, such as Remington's Pharmaceutical Sciences, Mack Publishing Company, Easton, Pa., 18$^{th}$ edition (1990).

For oral administration of inhibitors of EGFR kinase, FGFR kinase, or PDGFR kinase, tablets containing one or more than one active agent are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an inhibitor of EGFR kinase, FGFR kinase, or PDGFR kinase, in about 0.1% (w/v) to about 5% (w/v) concentration can be prepared.

For veterinary purposes, the active agents can be administered separately or together to animals using any of the forms and by any of the routes described above. In a preferred embodiment, the kinase inhibitor is administered in the form of a capsule, bolus, tablet, liquid drench, by injection or as an implant. As an alternative, the EGFR kinase inhibitor can be administered with the animal feedstuff, and for this purpose a concentrated feed additive or premix may be prepared for a normal animal feed. Such formulations are prepared in a conventional manner in accordance with standard veterinary practice.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGF receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. EGFR kinase inhibitors include anti-EGFR or anti-EGF aptamers, anti-EGFR or anti-EGF antibodies, soluble EGFR receptor decoys that prevent binding of a EGFR to its cognate receptor, or aptamers or antibodies that inhibit other EGFR ligands (e.g. TGF-α). In a preferred embodiment, the EGFR kinase inhibitor is a small organic molecule or an antibody that binds specifically to the human EGFR.

EGFR kinase inhibitors include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or TARCEVA® (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (TYKERB®; also known as GW-572016 or lapatinib ditosylate; GSK); and gefitinib (also known as ZD1839 or IRESSA®; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl)amine (i.e. erlotinib), its hydrochloride salt (i.e. erlotinib HCl, TARCEVA®), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX®; Imclone Systems), panitumumab (VECTIBIX®; Abgenix; also known as ABX-EGF), EMD 72000 (Merck KgaA, Darmstadt), RH3 (York Medical Bioscience Inc.), and MDX-447 (Medarex/Merck KgaA).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

As used herein, the term "PDGFR kinase inhibitor" refers to any PDGFR kinase inhibitor that is currently known in the art or that will be identified in the future, and includes any chemical entity that, upon administration to a patient, results in inhibition of a biological activity associated with activation of the PDGF receptor in the patient, including any of the downstream biological effects otherwise resulting from the binding to PDGFR of its natural ligand. Such PDGFR kinase inhibitors include any agent that can block PDGFR activation or any of the downstream biological effects of PDGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the PDGF receptor, thereby making the receptor inaccessible to its natural ligand so that its normal biological activity is prevented or reduced. Alternatively, such an inhibitor can act by modulating the dimerization of PDGFR polypeptides, or interaction of PDGFR polypeptide with other proteins, or enhance ubiquitination and endocytotic degradation of PDGFR. PDGFR kinase inhibitors include but are not limited to low molecular weight inhibitors, antibodies or antibody fragments, antisense constructs, small inhibitory RNAs (i.e. RNA interference by dsRNA; RNAi), and ribozymes. PDGFR kinase inhibitors include anti-PDGF or anti-PDGFR aptamers, anti-PDGF or anti-PDGFR antibodies, or soluble PDGF receptor decoys that prevent binding of a PDGF to its cognate receptor. In a preferred embodiment, the PDGFR kinase inhibitor is a small organic molecule or an antibody that binds specifically to the human PDGFR. The ability of a compound or agent to serve as a PDGFR kinase inhibitor may be determined according to the methods known in art and, further, as set forth in, e.g., Dai et al., (2001) Genes & Dev. 15: 1913-25; Zippel, et al., (1989) Eur. J. Cell Biol. 50(2):428-34; and Zwiller, et al., (1991) Oncogene 6: 219-21.

The invention includes PDGFR kinase inhibitors known in the art as well as those supported below and any and all equivalents that are within the scope of ordinary skill to create. For example, inhibitory antibodies directed against PDGF are known in the art, e.g., those described in U.S. Pat. Nos. 5,976,534, 5,833,986, 5,817,310, 5,882,644, 5,662,904, 5,620,687, 5,468,468, and PCT WO 2003/025019, the contents of which are incorporated by reference in their entirety. In addition, the invention includes N-phenyl-2-pyrimidine-amine derivatives that are PDGFR kinase inhibitors, such as those disclosed in U.S. Pat. No. 5,521,184, as well as WO2003/013541, WO2003/078404, WO2003/099771, WO2003/015282, and WO2004/05282 which are hereby incorporated in their entirety by reference.

Small molecules that block the action of PDGF are known in the art, e.g., those described in U.S. Pat. Nos. 6,528,526 (PDGFR tyrosine kinase inhibitors), 6,524,347 (PDGFR tyrosine kinase inhibitors), 6,482,834 (PDGFR tyrosine kinase inhibitors), 6,472,391 (PDGFR tyrosine kinase inhibitors), 6,949,563, 6,696,434, 6,331,555, 6,251,905, 6,245,760, 6,207,667, 5,990,141, 5,700,822, 5,618,837, 5,731,326, and 2005/0154014, and International Published Application Nos. WO 2005/021531, WO 2005/021544, and WO 2005/021537, the contents of which are incorporated by reference in their entirety.

Proteins and polypeptides that block the action of PDGF are known in the art, e.g., those described in U.S. Pat. Nos. 6,350,731 (PDGF peptide analogs), 5,952,304, the contents of which are incorporated by reference in their entirety.

Bis mono- and bicyclic aryl and heteroaryl compounds which inhibit EGF and/or PDGF receptor tyrosine kinase are known in the art, e.g., those described in, e.g. U.S. Pat. Nos. 5,476,851, 5,480,883, 5,656,643, 5,795,889, and 6,057,320, the contents of which are incorporated by reference in their entirety.

Antisense oligonucleotides for the inhibition of PDGF are known in the art, e.g., those described in U.S. Pat. Nos. 5,869,462, and 5,821,234, the contents of each of which are incorporated by reference in their entirety.

Aptamers (also known as nucleic acid ligands) for the inhibition of PDGF are known in the art, e.g., those described in, e.g., U.S. Pat. Nos. 6,582,918, 6,229,002, 6,207,816, 5,668,264, 5,674,685, and 5,723,594, the contents of each of which are incorporated by reference in their entirety.

Other compounds for inhibiting PDGF known in the art include those described in U.S. Pat. Nos. 5,238,950, 5,418, 135, 5,674,892, 5,693,610, 5,700,822, 5,700,823, 5,728,726, 5,795,910, 5,817,310, 5,872,218, 5,932,580, 5,932,602, 5,958,959, 5,990,141, 6,358,954, 6,537,988 and 6,673,798, the contents of each of which are incorporated by reference in their entirety.

A number of types of tyrosine kinase inhibitors that are selective for tyrosine kinase receptor enzymes such as PDGFR are known (see, e.g., Spada and Myers ((1995) Exp. Opin. Ther. Patents, 5: 805) and Bridges ((1995) Exp. Opin. Ther. Patents, 5: 1245). Additionally Law and Lydon have summarized the anticancer potential of tyrosine kinase inhibitors ((1996) Emerging Drugs: The Prospect For Improved Medicines, 241-260). For example, U.S. Pat. No. 6,528,526 describes substituted quinoxaline compounds that selectively inhibit platelet-derived growth factor-receptor (PDGFR) tyrosine kinase activity. The known inhibitors of PDGFR tyrosine kinase activity includes quinoline-based inhibitors reported by Maguire et al., ((1994) J. Med. Chem., 37: 2129), and by Dolle, et al., ((1994) J. Med. Chem., 37: 2627). A class of phenylamino-pyrimidine-based inhibitors was recently reported by Traxler, et al., in EP 564409 and by Zimmerman et al., ((1996) Biorg. Med. Chem. Lett., 6: 1221-1226) and by Buchdunger, et al., ((1995) Proc. Nat. Acad. Sci. (USA), 92: 2558). Quinazoline derivatives that are useful in inhibiting PDGF receptor tyrosine kinase activity include bismono- and bicyclic aryl compounds and heteroaryl compounds (see, e.g., WO 92/20642), quinoxaline derivatives (see (1994) Cancer Res., 54: 6106-6114), pyrimidine derivatives (Japanese Published Patent Application No. 87834/94) and dimethoxyquinoline derivatives (see Abstracts of the 116th Annual Meeting of the Pharmaceutical Society of Japan (Kanazawa), (1996), 2, p. 275, 29(C2) 15-2).

Specific preferred examples of low molecular weight PDGFR kinase inhibitors that can be used according to the present invention include Imatinib (GLEEVEC®; Novartis); SU-12248 (sunitib malate, SUTENT®; Pfizer); Dasatinib (SPRYCEL®; BMS; also known as BMS-354825); Sorafenib (NEXAVAR®; Bayer; also known as Bay-43-9006); AG-13736 (Axitinib; Pfizer); RPR127963 (Sanofi-Aventis); CP-868596 (Pfizer/OSI Pharmaceuticals); MLN-518 (tandutinib; Millennium Pharmaceuticals); AMG-706 (Motesanib; Amgen); ARAVA® (leflunomide; Sanofi-Aventis; also known as SU101), and OSI-930 (OSI Pharmaceuticals);

Additional preferred examples of low molecular weight PDGFR kinase inhibitors that are also FGFR kinase inhibitors that can be used according to the present invention include XL-999 (Exelixis); SU6668 (Pfizer); CHIR-258/TKI-258 (Chiron); RO4383596 (Hoffmann-La Roche) and BIBF-1120 (Boehringer Ingelheim).

As used herein, the term "FGFR kinase inhibitor" refers to any FGFR kinase inhibitor that is currently known in the art or that will be identified in the future, and includes any chemical entity that, upon administration to a patient, results in inhibition of a biological activity associated with activation of the FGF receptor in the patient, including any of the downstream biological effects otherwise resulting from the binding to FGFR of its natural ligand. Such FGFR kinase inhibitors include any agent that can block FGFR activation or any of the downstream biological effects of FGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the FGF receptor, thereby making the receptor inaccessible to its natural ligand so that its normal biological activity is prevented or reduced. Alternatively, such an inhibitor can act by modulating the dimerization of FGFR polypeptides, or interaction of FGFR polypeptide with other proteins, or enhance ubiquitination and endocytotic degradation of FGFR. FGFR kinase inhibitors include but are not limited to low molecular weight inhibitors, antibodies or antibody fragments, antisense constructs, small inhibitory RNAs (i.e. RNA interference by dsRNA; RNAi), and ribozymes. FGFR kinase inhibitors include anti-FGF or anti-FGFR aptamers, anti-FGF or anti-FGFR antibodies, or soluble FGFR receptor decoys that prevent binding of a FGFR to its cognate receptor. In a preferred embodiment, the FGFR kinase inhibitor is a small organic molecule or an antibody that binds specifically to the human FGFR. Anti-FGFR antibodies include FR1-H7 (FGFR-1) and FR3-D11 (FGFR-3) (Imclone Systems, Inc.).

FGFR kinase inhibitors also include compounds that inhibit FGFR signal transduction by affecting the ability of heparan sulfate proteoglycans to modulate FGFR activity. Heparan sulfate proteoglycans in the extracellular matrix can mediate the actions of FGF, e.g., protection from proteolysis, localization, storage, and internalization of growth factors (Faham, S. et al. (1998) Curr. Opin. Struct. Biol., 8:578-586), and may serve as low affinity FGF receptors that act to present FGF to its cognate FGFR, and/or to facilitate receptor oligomerization (Galzie, Z. et al. (1997) Biochem. Cell. Biol., 75:669-685).

The invention includes FGFR kinase inhibitors known in the art (e.g. PD173074) as well as those supported below and any and all equivalents that are within the scope of ordinary skill to create.

Examples of chemicals that may antagonize FGF action, and can thus be used as FGFR kinase inhibitors in the methods described herein, include suramin, structural analogs of suramin, pentosan polysulfate, scopolamine, angiostatin, sprouty, estradiol, carboxymethylbenzylamine dextran (CMDB7), suradista, insulin-like growth factor binding protein-3, ethanol, heparin (e.g., 6-O-desulfated heparin), low molecular weight heparin, protamine sulfate, cyclosporin A, or RNA ligands for bFGF.

Other agents or compounds for inhibiting FGFR kinase known in the art include those described in U.S. Pat. Nos. 7,151,176 (Bristol-Myers Squibb Company; Pyrrolotriazine compounds); 7,102,002 (Bristol-Myers Squibb Company; pyrrolotriazine compounds); 5,132,408 (Salk Institute; peptide FGF antagonists); and 5,945,422 (Warner-Lambert Company; 2-amino-substituted pyrido[2,3-d]pyrimidines); U.S. published Patent application Nos. 2005/0256154 (4-amino-thieno[3,2-c]pyridine-7-carboxylic acid amide compounds); and 2004/0204427 (pyrimidino compounds); and published International Patent Applications WO-2007019884 (Merck Patent GmbH; N-(3-pyrazolyl)-N'-4-(4-pyridinyloxy)phenyl)urea compounds); WO-2007009773 (Novartis AG; pyrazolo[1,5-a]pyrimidin-7-yl amine derivatives); WO-2007014123 (Five Prime Therapeutics, Inc.; FGFR fusion proteins); WO-2006134989 (Kyowa Hakko Kogyo Co., Ltd.; nitrogenous heterocycle compounds); WO-2006112479 (Kyowa Hakko Kogyo Co., Ltd.; azaheterocycles); WO-2006108482 (Merck Patent GmbH; 9-(4-ureidophenyl)purine compounds); WO-2006105844 (Merck Patent GmbH; N-(3-pyrazolyl)-N'-4-(4-pyridinyloxy)phenyl)urea compounds); WO-2006094600 (Merck Patent GmbH; tetrahydropyrrolo-quinoline derivatives); WO-2006050800 (Merck Patent GmbH; N,N'-diarylurea derivatives); WO-2006050779 (Merck Patent GmbH; N,N'-diarylurea derivatives); WO-2006042599 (Merck Patent GmbH; phenylurea derivatives); WO-2005066211 (Five Prime Therapeutics, Inc.; anti-FGFR antibodies); WO-2005054246 (Merck Patent GmbH; heterocyclyl amines); WO-2005028448 (Merck Patent GmbH; 2-amino-1-benzyl-substituted benzimidazole derivatives); WO-2005011597 (Irm Llc; substituted heterocyclic derivatives); WO-2004093812 (Irm Llc/Scripps; 6-phenyl-7H-pyrrolo[2,3-d]pyrimidine derivatives); WO-2004046152 (F. Hoffmann La Roche AG; pyrimido[4,5-e]oxadiazine derivatives); WO-2004041822 (F. Hoffmann La Roche AG; pyrimido[4,5-d]pyrimidine derivatives); WO-2004018472 (F. Hoffmann La Roche AG; pyrimido[4,5-d]pyrimidine derivatives); WO-2004013145 (Bristol-Myers Squibb Company; pyrrolotriazine derivatives); WO-2004009784 (Bristol-Myers Squibb Company; pyrrolo[2,1-f][1,2,4]triazin-6-yl compounds); WO-2004009601 (Bristol-Myers Squibb Company; azaindole compounds); WO-2004001059 (Bristol-Myers Squibb Company; heterocyclic derivatives); WO-02102972 (Prochon Biotech Ltd./Morphosys AG; anti-FGFR antibodies); WO-02102973 (Prochon Biotech Ltd.; anti-FGFR antibodies); WO-00212238 (Warner-Lambert Company; 2-(pyridin-4-ylamino)-6-dialkoxyphenyl-pyrido [2,3-d]pyrimidin-7-one derivatives); WO-00170977 (Amgen, Inc.; FGFR-L and derivatives); WO-00132653 (Cephalon, Inc.; pyrazolone derivatives); WO-00046380 (Chiron Corporation; FGFR-Ig fusion proteins); and WO-00015781 (Eli Lilly; polypeptides related to the human SPROUTY-1 protein).

Specific preferred examples of low molecular weight FGFR kinase inhibitors that can be used according to the present invention include RO-4396686 (Hoffmann-La Roche); CHIR-258 (Chiron; also known as TKI-258); PD 173074 (Pfizer); PD 166866 (Pfizer); ENK-834 and ENK-835 (both Enkam Pharmaceuticals A/S); and SU5402 (Pfizer). Additional preferred examples of low molecular weight FGFR kinase inhibitors that are also PDGFR kinase inhibitors that can be used according to the present invention include XL-999 (Exelixis); SU6668 (Pfizer); CHIR-258/TKI-258 (Chiron); R04383596 (Hoffmann-La Roche), and BIBF-1120 (Boehringer Ingelheim).

In the context of the methods of treatment of this invention, inhibitors of EGFR kinase, FGFR kinase, or PDGFR kinase, are used as a composition comprised of a pharmaceutically acceptable carrier and a non-toxic therapeutically effective amount of the kinase inhibitor compound (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Pharmaceutical compositions used in the present invention comprising an kinase inhibitor compound (including pharmaceutically acceptable salts thereof) as active ingredient, can include a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the kinase inhibitor compounds (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an EGFR kinase, FGFR kinase, or PDGFR kinase inhibitor compound (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

An EGFR kinase, FGFR kinase, or PDGFR kinase inhibitor compound (including pharmaceutically acceptable salts thereof) used in this invention, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, the pharmaceutical composition can comprise a kinase inhibitor compound in combination with an anticancer agent, wherein said anticancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition used for this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions for the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a kinase inhibitor compound (including pharmaceutically acceptable salts thereof), via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions for this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a kinase inhibitor compound (including pharmaceutically acceptable salts thereof) may also be prepared in powder or liquid concentrate form.

Dosage levels for the compounds used for practicing this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons. (e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Academic Press, Inc. (e.g. ISBN 0-12-213585-7)), or as described in the many university and commercial websites devoted to describing experimental methods in molecular biology.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

Experimental Details.

Materials and Methods.

Cell Culture and Preparation of Cell Extracts.

The human NSCLC lines H1299, H266, H522, H650, H1437, H1155, Calu1, Hop92, H23, H292, H358, H322, H441, A549, Calu6, H460, H1703 and SW1573 were cultured in the appropriate ATCC recommended supplemented media. Cell extracts were prepared by detergent lysis (50 mM Tris-HCl, pH8, 150 mM NaCl, 1% NP-40, 0.5% NaDeoxycholate, 0.1% SDS) containing protease and phosphatase inhibitors. The soluble protein concentration was determined by micro-BSA assay (Pierce, Rockford Ill.). In experiments monitoring serum stimulation, cells were grown in media with 0.5% FBS for 24 hours followed by addition of FBS to a final concentration of 10% for 10 minutes prior to lysis. In experiments where inhibitor treatment was required, inhibitor was added at the indicated concentration and the cells the stimulated with the indicated ligand. For cell proliferation assays cells were plated, inhibitor added and proliferation measured after 72 hours using the CELLTITERGLO™ cell viability assay (Promega, Madison Wis.).

In Vivo Pharmacology.

Female CD-1 nu/nu mice (Charles River Laboratories, Wilmington, Mass.) were implanted with harvested NSCLC tumor cells in a single subcutaneous site on the flank of the mice in the axillary region. Tumors were allowed to grow to 200±50 mm$^3$, at which time the animals were sorted into treatment groups of 8 animals per group based on weight (±1 g body weight) and tattooed on the tail for permanent identification. Tumor volumes and body weights were determined twice weekly. The tumor volume was determined by measuring in two directions with vernier calipers and calculated using the formula: Tumor volume=(length×width$^2$)/2. The data were plotted as the % change in mean values of tumor volume and body weight for each group. The tumor growth inhibition (% TGI) was determined as % TGI=100(1−$W_t$−$W_c$): where $W_t$ is the median tumor volume of the treated group at time x and $W_c$ is the median tumor volume of the control group at time x. TARCEVA® was dosed in a 6%

Captisol (CyDex, Inc) in WFI (Water for Injection) solution and all control animals were dosed with an equal volume of the vehicle. Tumor growth inhibition studies were dosed by oral gavage once a day for 14 days. Pharmacodynamic studies were dosed by oral gavage for 1-3 days with tumors from 4 control and 4 TARCEVA® treated animals harvested and snap frozen in liquid nitrogen 4 hours after dosing on Days 1, 2 and 3.

Protein Immunodetection.

Protein immunodetection was performed by electrophoretic transfer of SDS-PAGE separated proteins to nitrocellulose, incubation with antibody and chemiluminescent detection (PicoWest; Pierce, Rockford, Ill.). Antibodies used were as follows: Phospho-Akt$^{S473}$ (Cell Signaling, Beverly, Mass.; #9271), Akt (Cell Signaling, Beverly, Mass.; #9272), Phospho-p44/42 Map kinase$^{T202/Y204}$ (Erk1/2; Cell Signaling, Beverly, Mass.; #9101), p44/42 MAP kinase (Cell Signaling, Beverly, Mass.; #9102), β-actin (Sigma-Aldrich, St. Louis, Mo.; #A5441), PDGFRα (Cell Signaling, Beverly, Mass.; #3164), PDGFRβ (Cell Signaling, Beverly, Mass.; #3961), FGFR2 (Santa Cruz Biotechnology, Inc., Santa Cruz, Calif.; #sc122), FGFR3 (Santa Cruz Biotechnology, Inc., Santa Cruz, Calif.; #sc123), FGFR4 (Santa Cruz Biotechnology, Inc., Santa Cruz, Calif.; #sc124), E-cadherin (Santa Cruz, #sc21791), Cytokeratin 8/18 (AbCam, Cambridge, Mass.; 8477), Vimentin (BD Biosciences, San Jose, Calif.; #550513), GAPDH (Santa Cruz Biotechnology, Inc., Santa Cruz, Calif.; #sc25778).

RNA Isolation and RT-PCR Analysis of Gene Expression.

Total RNA was isolated from cell lines using the Qiagen RNeasy kit (Qiagen, #74104). First strand cDNA was synthesized and PCR of the gene of interest was carried out using a commercial RT-PCR kit (Perkin Elmer, N808-0236) and the appropriate taqman probe (see Table 1) on an Applied Biosystems 7300 real time PCR machine.

TABLE 1

Taqman Probes used for Gene Expression Studies

| Gene | Applied Biosystems Order No. |
| --- | --- |
| TGFBR1 | Hs00610319_m1 |
| TGFBR2 | Hs00234253_m1 |
| TGFB1 | Hs00234244_m1 |
| TGFB2 | Hs00234244_m1 |
| TGFB3 | Hs00234245_m1 |
| ALK3 | Hs00831730_s1 |
| ALK6 | Hs00176144_m1 |
| PDGFRa | Hs00183486_m1 |
| PDGFRb | Hs00182163_m1 |
| PDGFa | Hs00234994_m1 |
| PDGFb | Hs00234042_m1 |
| FGFR1 | Hs00241111_m1 |
| FGFR2 | Hs00240792_m1 |
| IGFR1 | Hs00181385_m1 |
| IGF1 | Hs00153126_m1 |
| IGF2 | Hs00171254_m1 |
| TGFa | Hs00177401_m1 |
| EPREG | Hs00914313_m1 |
| AREG | Hs00155832_m1 |
| NRG1 | Hs00247620_m1 |
| NRG2 | Hs00171706_m1 |
| BTC | Hs00156140_m1 |
| GAPDH | Hs99999905_m1 |

Immunohistochemical Staining of Xenograft and Human Tissue Samples.

Xenograft tumors grown in nude mice were harvested and sections embedded in serial sections were cut from the tumor block and a tissue microarray prepared. A human NSCLC tissue microarray was prepared in the same manner. (HistoRx, Yale Conn.). The tissue sections were de-paraffinized first by heating at 60° C., then by two xylene rinses followed by two rinses with 100% ethanol and a rinse in water. Antigen retrieval was performed with a sodium citrate buffer at a pH of 6.0 in the PT Module device (LabVision, Fremont, Calif.). After rinsing briefly in 1×Tris-buffered saline (TBS), a 30-minute incubation with 2.5% hydrogen peroxide/methanol was used to block endogenous peroxidases. In order to reduce non-specific background staining, slides were incubated with 0.3% Bovine serum albumin (BSA)/1×TBS for one hour at room temperature, followed by a series rinses in 1×TBS and 1×TBS/0.01% Triton (TBS washes). Slides were incubated overnight at 4° C. with either a monoclonal mouse anti-cytokeratin antibody (clone AE1/AE3, DAKO, Carpinteria, Calif., 1:200; specific for keratins 1, 2, 3, 4, 5, 6, 7, 8, 10, 13, 14, 15, 16, and 19 (Moll's designation)) when using a rabbit primary target antibody or with a rabbit anti-cytokeratin antibody (Wide Spectrum Screening, 1:200, DAKO, Carpinteria, Calif.; binds to a wide variety of epithelial keratins) when using a monoclonal mouse primary target antibody. Slides were washed in 1×TBS rinses following overnight primary antibody incubation followed by secondary antibodies for 1 hour at room temperature as follows: Alexa 555 goat anti-mouse or Alexa 555 goat anti-rabbit (1:200, Molecular Probes, Eugene, Oreg.) for detecting cytokeratin, and species specific horseradish peroxidase (HRP) with a dextran-polymer backbone (Envision, DAKO, Carpinteria, Calif.) followed by Cy-5 tyramide (1:50, Perkin Elmer, Waltham, Mass.) coupling to the HRP for detection of the target primary antibodies. Cy5 was used for the target antibodies because its emission peak is outside the spectrum of tissue autofluorescence. 4',6-diamidino-2-phenylindole/ DAPI (Prolong Gold Anti fade w/DAPI mounting gel, Molecular Probes, Eugene, Oreg.) was utilized as nuclear marker.

Assessment of Cytokeratin Expression

When referring to assessment of keratin levels herein when the expression levels of one or more epithelial keratins are simultaneously assessed (e.g. by using an antibody preparation that binds to multiple keratins), the assessed keratins are generally referred to either by the specific names of the proteins being assessed (e.g. "cytokeratin 8/18" or "cytokeratin 8 and/or cytokeratin 18", determined for example by an antibody preparation containing antibodies to cytokeratins 8 and 18) or just by the term "cytokeratin" (e.g. when one or more keratins are assessed by a pan-specific antibody).

Results

EGF receptor (EGFR) has been shown to be overexpressed in human cancers including lung (NSCLC), CNS, head and neck, bladder, pancreas and breast and overexpression has been shown to correlate with poor survival (Yarden Y. and Sliwkowski M X. Nature Reviews (2001) 2:127-137.). Inhibitors of EGFR function have shown clinical utility and the definition of key EGFR signaling pathways which describe patient subsets most likely to benefit from therapy has become an important area of investigation. Though paracrine and autocrine activation of EGFR plays a critical role in the maintenance of epithelial tissues, NSCLC lines show considerable variability in their cellular responses to EGFR inhibition and can be relatively insensitive to pharmacological withdrawal of EGFR signaling. The role of EGFR mutations (Lynch T J, et al. The New England Journal of Medicine (2004) 350:2129-2139; Sordella R, et al. Science (2004) 305: 1163-1167) as a principle mechanism in conferring sensitivity to EGFR inhibitors has been controversial (Shepherd F A, et al. The New England Journal of Medicine (2005) 353:123-132.). The variable sensitivities to EGFR inhibition of both cell lines and tumors containing wild-type EGFR, has been shown to derive in part from EGFR-independent activation of the phosphatidylinositol-3' kinase pathway, leading to a continued phosphorylation of the anti-apoptotic serine-threonine kinase Akt (Vivanco I, and Sawyers C L. Nat Rev Cancer (2002) 2:489-501.). The molecular determinants to alternative routes of PI-3' kinase activation and consequent EGFR inhibitor insensitivity are poorly described, although the insulin-like growth factor-1 receptor, which strongly activates the PI-3' kinase pathway, has been implicated in cellular resistance to EGF inhibitors (Chakravarti A, et al. Cancer Res (2002) 62:200-207). Recent clinical data also suggest EGFR gene amplification as measured by FISH and EGFR protein as measured by immunohistochemical methods correlate with NSCLC patient benefit to EGFR inhibitors (Cappuzzo F., et al. J Natl Cancer Inst (2005) 97(9):643-655; Hirsch F R. and Witta S. Curr Opin Oncol (2005) 17(2):118-122).

Here it is demonstrated that human NSCLC cells containing wild-type EGFR show a variable sensitivity to erlotinib treatment in vitro and in vivo. Sensitivity to EGFR inhibition did not correlate with total EGFR levels, but did correlate with phospho-EGFR, phospho-ErbB3 and with total ErbB3. The sensitivity of the cells and xenografts to erlotinib treatment can be predicted by whether the cells have undergone a process termed epithelial-mesenchymal transition (EMT). This transition is characterized by the combined loss of epithelial cell junction proteins such as E-cadherin and the gain of mesenchymal markers such as vimentin or fibronectin (Thiery J P. Curr Opin Cell Biol (2003) 15(6):740-746.). It has become increasingly clear over recent years that EMT, already established as a critical developmental process, plays a major role in the progression of cancer (Grunert S, et al. Nat Rev Mol Cell Biol (2003) 4(8):657-665; Thiery J P. Nat Rev Cancer (2002) 2(6):442-454).

The data described herein demonstrates that a new mesenchymal-like tumor cell type has been identified, co-expressing the epithelial cell markers cytokeratin 8 and/or cytokeratin 18 and the mesenchymal cell marker vimentin. These unusual mesenchymal-like 'hybrid' tumor cells have unexpected properties and are sensitive to new anti-cancer treatments.

Figure 9:
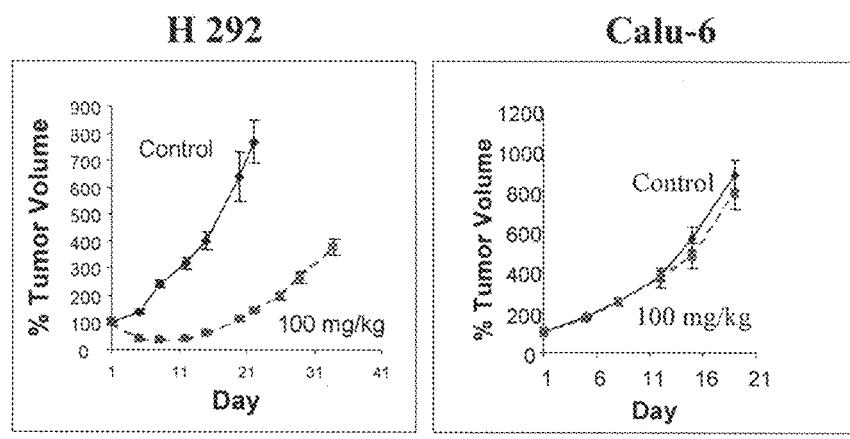
FIG. 9: Sensitivity of NSCLC cell lines to erlotinib In Vivo. Female CD-1 nu/nu mice were implanted with H292 or Calu6 cells and tumor allowed to grow to 200 mm$^3$. Animals were then either left untreated or treated with 100 mg/kg erlotinib once a day for 14 days. Tumor volume was measured twice weekly.

Xenograft growth of H292 and Calu6 NSCLC lines with and without the EGFR kinase inhibitor erlotinib indicated that H292 is sensitive to EGFR inhibition and shows a reduction in tumor volume during the dosing period, while Calu6 is insensitive to EGFR inhibition (FIG. 9). Calu6 has undergone an EMT-like transition and has become relatively insensitive to EGFR inhibition.

Figure 10:
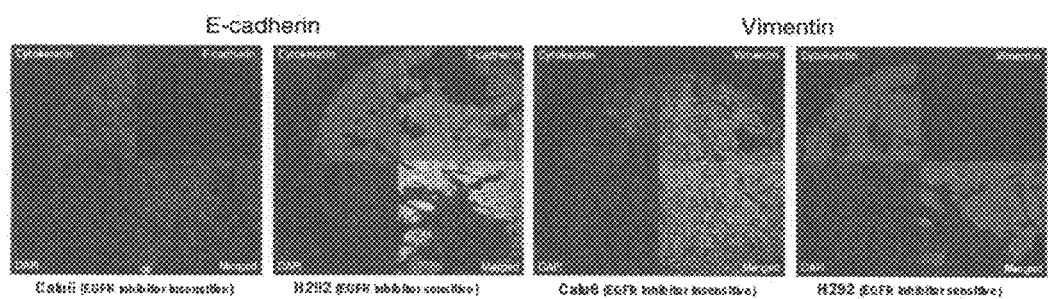
FIG. 10: Multiplex immunohistochemical staining of NSCLC Xenograft sections. Calu6 and H292 cells were used to grow tumors in nude mice. The tumors were harvested and preserved in paraformaldehyde before section were cut. Individual sections were stained with DAPI (lower left) and anti-cytokeration (upper left) and either anti-E-caherin or anti-vimentin antibodies (upper right). A merged representation of all three stains is shown in the lower right panel.
Figure 11:
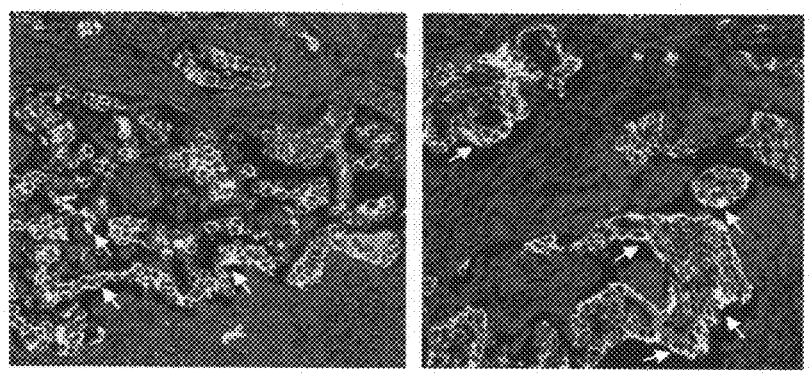
FIG. 11: Multiplex staining of human NSCLC tissue. NSCLC patient biopsy samples were paraffin embedded and sections cut to generate a tissue microarray (TMA). The TMA was stained with antibodies directed against Cytokeratin and Vimentin and the images shown are a merged image of both stains. The areas indicated by arrows are selected regions of overlap of both antibody stains, indicating co-expression of cytokeratin and vimentin.
Figure 12:
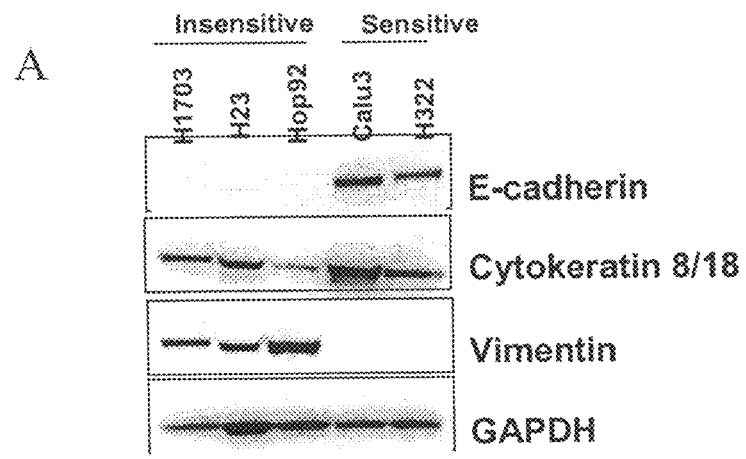
FIG. 12: Coexpression of cytokeratin and vimentin in mesenchymal-like NSCLC cell lines. A. Protein extracts were prepared from the indicated NSCLC cell lines and immunoblots carried out with the indicated anitbodies. The erlotinib-insensitive cell lines (H1703, H23 and Hop92) express both cytokeration 8/18 and vimentin. B. Graphical representation of the western blot shown in A.
Figure 12:
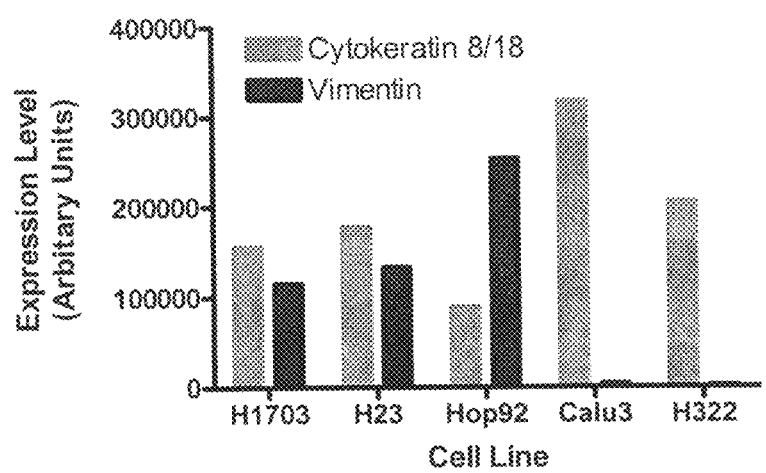

E-cadherin, cytokeratin and vimentin protein expression was measured by fluorescent immunohistochemistry in NSCLC xenografts, either sensitive or insensitive to EGFR inhibition (FIG. 10). A comparison of the NSCLC xenografts H292 (sensitive) and Calu6 (insensitive) was made. The left two panels examine E-cadherin staining, where E-cadherin is stained with a red fluorescent antibody, cytokeratin is stained green and the cell nuclei are stained blue with DAPI. The right two panels examine vimentin staining where vimentin is stained with a red fluorescent antibody, cytokeratin is stained green and the cell nuclei are stained blue with DAPI. The following observations were made. Cytokeratin is reduced but not abolished in EGFR inhibitor insensitive cells having undergone an EMT-like transition. Vimentin is a marker of mesenchymal cell lineages, while cytokeratin is a marker of epithelial cells. Mesenchymal-like 'hybrid' tumor cells are distinguished by stable expression of both vimentin and cytokeratins (8 and/or 18) within a single tumor cell. This can also be observed in non-small cell lung cancer again by dual labeling of single tumor cells with pan-cytokeratin and vimentin antibodies in an IHC format (FIG. 11). Epithelial markers are cytokeratin (red); the mesenchymal marker is vimentin (green). The co-staining 'hybrid'—tumor cells contain both vimentin and cytokeratin (yellow), and example regions are indicated by the arrows (FIG. 11).

Figure 7:
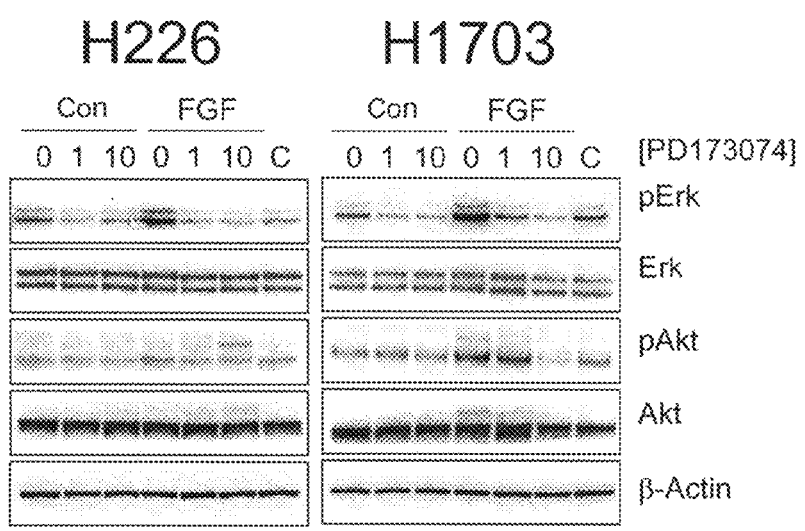
FIG. 7: Inhibition of FGFR Signaling in H1703 and H226 NSCLC Cells. H1703 and H226 cells were treated with either 1 or 10M PD173074 for 2 hours and then left untreated (CON) or treated with 10 ng/ml FGF for 15 min (FGF). Cell lysates were prepared and immunoblots using antibodies against pERK, total ERK, pAKT (ser473), total AKT and β-actin were performed.

These mesenchymal-like 'hybrid' tumor cells have acquired unusual dependence on growth factor receptor pathways not seen in normal epithelial cells and not previously described in tumor cells. For example these tumor cells have acquired the expression of FGF and PDGF receptors. Furthermore, they can respond to PDGFs and FGFs in an autocrine or paracrine manner to activate the PI-3 kinase, ras/raf/mek/erk and STAT3/5 pathways (FIGS. 3B and 7). The 'hybrid' cells are frequently exquisitely sensitive to PDGF receptor and/or FGF receptor kinase inhibitors as measured by proliferation and/or migration.

Some hybrid-like tumor cells express PDGFR and/or FGFR but fail to make the respective ligands in an autocrine manner. However, in vivo such newly acquired receptors can respond to PDGFs and FGFs presented by nearby stromal cells (e.g. fibroblasts, glia, endothelial cells and inflammatory cells) to promote tumor metastasis and migration. Inhibitors of PDGF and FGF receptors were shown to inhibit these processes in hybrid tumor cells and are predicted to improve cancer patient survival in tumors containing such hybrid tumor cells co-expressing vimentin and one or more cytokeratins.

Proteins associated with survival signaling and epithelial-mesenchymal cell phenotypes were isolated and measured by multiple experimental approaches. These included mass spectrometry, immunoblot and confocal microscopy measurements comparing individual protein abundance between NSCLC tumor lines.

Hybrid Epithelial-Mesenchymal Tumor Cells

Examination of the proteins and pathways exploited by tumor cells reveal a new hybrid cell type with epithelial and mesenchymal characteristics. Hybrid tumor cells simultaneously express the epithelial keratins (e.g. cytokeratin 8 and/or 18) and the mesenchymal marker vimentin. The use of PDGFR and FGFR inhibitors to inhibit mesenchymal-like hybrid tumor cells is proposed.

In order to understand the biology of the mesenchymal-like NSCLC cell lines in more detail the expression patterns of a number of different receptor tyrosine kinases and their ligands were profiled. The cell lines used are detailed in Table 2.

TABLE 2

Sensitivity of Tumor Cells to EGFR Kinase Inhibitors

| NSCLC Cell line | Phenotype* | Erlotinib Senistivity |
| --- | --- | --- |
| CALU1 | Mesenchymal-like | Insensitive |
| H23 | Mesenchymal-like | Insensitive |
| H226 | Mesenchymal-like | Insensitive |
| H522 | Mesenchymal-like | Insensitive |
| H650 | Mesenchymal-like | Insensitive |
| H1155 | Mesenchymal-like | Insensitive |
| H1299 | Mesenchymal-like | Insensitive |
| H1437 | Epithelial | Insensitive |
| HOP92 | Mesenchymal-like | Insensitive |
| H1703 | Mesenchymal-like | Insensitive |
| SW1573 | Mesenchymal-like | Insensitive |
| H460 | Mesenchymal-like | Insensitive |
| CALU6 | Mesenchymal-like | Insensitive |
| A549 | Mixed | Intermediate |
| H441 | Epithelial | Sensitive |
| H358 | Epithelial | Sensitive |

TABLE 2-continued

Sensitivity of Tumor Cells to EGFR Kinase Inhibitors

| NSCLC Cell line | Phenotype* | Erlotinib Sensitivity |
|---|---|---|
| H322 | Epithelial | Sensitive |
| H292 | Epithelial | Sensitive |

*Defined by expression of E-cadherin (Epithelial) or vimentin (Mesenchymal-like)

PDGFR Signaling in NSCLC

In order to understand the biology of the mesenchymal-like NSCLC cell lines in more detail the expression levels of the 2 members of the PDGF receptor family ($\alpha$ and $\beta$) as well as the ligands for these receptors (PDGFa and PDGFb) was profiled. FIG. 1 shows the results from a quantitative PCR assay using Taqman probes specific for the genes indicated. The results are shown as an average of duplicate experiments.

Analysis of the panel of NSCLC cell lines indicated that all of the cells produced PDGF ligands, irrespective of whether their phenotype was mesenchymal-like or epithelial. The mesenchymal-like cell line H1703 produced large amounts of PDGFb. Interestingly, none of the four epithelial cell lines expressed either PDGFR$\alpha$ or PDGFR$\beta$, whereas 8/13 of the mesenchymal-like lines expressed one or other of the receptors. Most notably, H1703 expressed large levels of PDGFRa. These results suggest that the mesenchymal-like cells lines have gained expression of PDGF receptors and potentially signal in an autocrine fashion.

Figure 2:
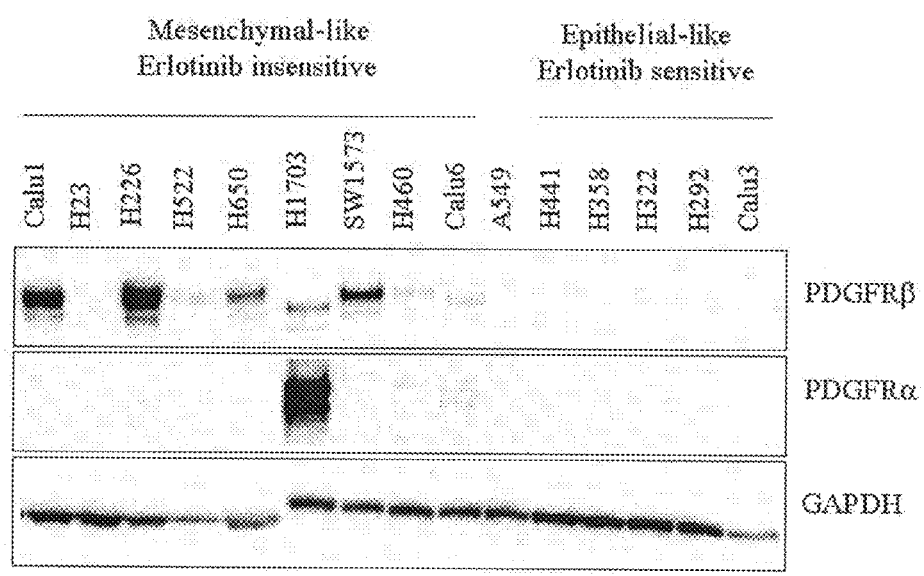
FIG. 2: Increased PDGF Receptor Expression in Mesenchymal-like NSCLC. Protein extracts were prepared from the indicated NSCLC cell lines. Lysates were separated by SDS-PAGE and transferred to nitrocellulose membrane. The membrane was probed with either anti-PDGFRα or anti-PDGFRβ antibodies.

As confirmation of the analysis at the mRNA level western blots were probed with antibodies against PDGFR$\alpha$ or PDGFR$\beta$ (FIG. 2). This confirmed that none of the epithelial cell lines expressed either PDGFR$\alpha$ or PDGFR$\beta$. Expression of PDGFR$\alpha$ was restricted to H1703 cells, but PDGFR$\beta$ was expressed to some extent in all of the mesenchymal-like lines analysed.

Collectively these results indicate that the mesenchymal-like cells, as part of their epithelial to mesenchymal transition, have gained expression of PDGF receptors and are likely to be utilizing this receptor signaling axis to mediate proliferation and/or survival signals. Therefore, the ability of PDGFR inhibitors to inhibit proliferation of these cell lines was tested. The inhibitor OSI-930 (OSI Pharmaceuticals, Melville, N.Y.) was utilized. This is a dual Kit/KDR inhibitor, which also shows relatively good potency against PDGF receptors.

Figure 3:
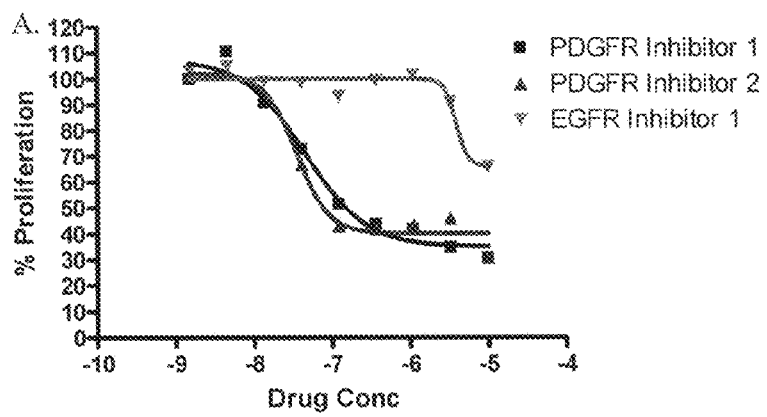
FIG. 3: Inhibition of PDGFR activity in NSCLC. A. H1703 cells were treated with increasing concentrations of PDGFR inhibitor 1 (OSI-930) (■), PDGFR inhibitor 2 (▲) or an EGFR inhibitor (erlotinib) (▼). After 72 hours incubation proliferation of the cells was measured by CellTitreGlo assay and plotted as a % proliferation relative to untreated cells. B. H1703 cells were treated with the PDGFR inhibitor OSI-930 for 2 hours and then left untreated or treated with PDGF (10 ng/ml) for 15 mins. Protein extracts were prepared and immunoblots probed with the indicated antibodies C. H1703 and Calu1 cells were treated with either 1 or 5 μM of PDGFR inhibitor OSI-930 and the effect on closure of the wound analysed after 24 hrs.
Figure 3:
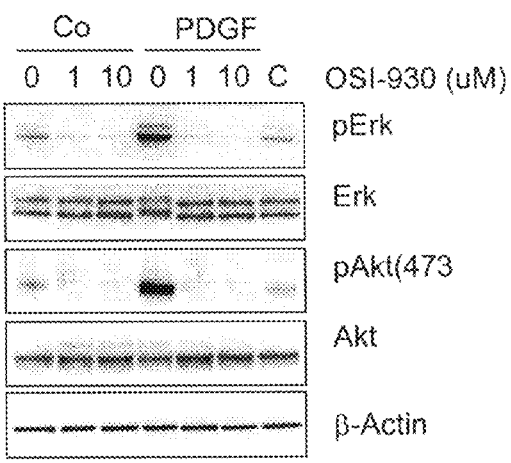
Figure 3:
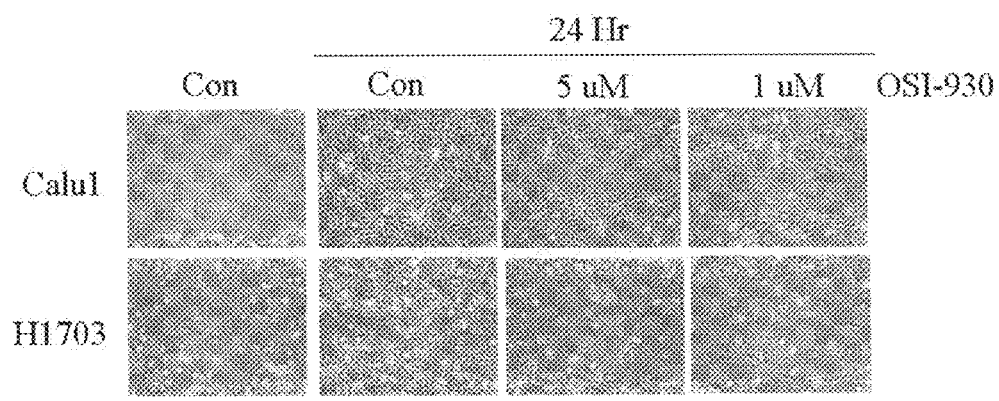

Three mesenchymal-like cell lines (H1703, Calu1 and H226) and one epithelial cell line (H358) were treated with increasing concentrations of OSI-930 in 10% FCS (FIG. 3) and cell proliferation assayed using CellTitreGlo. Inhibition of cell growth by OSI930 was only observed in H1703 cells. H1703 cells produce large amounts of ligand, suggesting that the inhibitor was working by inhibiting autocrine PDGFR signaling. Although the other cell lines (H226 and Calu1) contain high levels of PDGFR$\beta$ they are not growth inhibited by the PDGFR inhibitor. This may be due to there being insufficient activating ligand present in this cell culture system (N.B. PDGFR$\beta$ receptor dimer is only activated by PDGF-BB, not PDGF-AB or PDGF-AA). However, ligand will likely be available from paracrine signaling in human tumor tissue. In order to address this question, the cells were grown with 0.5% FCS and PDGF (mixed AA, AB and BB forms) added to the media to more closely model paracrine PDGF signaling. However, although H1703 cells were inhibited more potently under these conditions by OSI-930, the other cell lines failed to show any enhanced growth inhibition in monolayer tissue culture (FIG. 3A). The intracellular signaling pathways (ERK MAP kinase and AKT) were both inhibited in H1703 cells treated with the PDGFR inhibitor OSI-930 (FIG. 3B). The inhibitor reduced phosphorylation of ERK MAP kinase and AKT (on serine 473) under basal (10% FCS) and ligand stimulated conditions. The H226 cell line, expressing the PDGFR$\beta$ receptor but the incorrect ligand (i.e. not PDGF-BB, the primary activating ligand for PDGFR-$\beta\beta$), only showed ligand induced inhibition of ERK and AKT pathways. Both H1703 and Calu1 showed inhibition of cell motility in response to the PDGFR inhibitor OSI-930 (FIG. 3C).

Collectively these data indicate that the gain of PDGF receptor expression is a marker for cells that have undergone EMT and are now insensitive to EGFR pathway inhibition. It seems apparent that H1703 depends upon the PDGFR pathway for proliferation and survival pathways, with inhibition of the PDGFR$\alpha$ receptor providing a strong growth inhibitory response. The other mesenchymal-like cell lines which express the PDGFR$\beta$ receptor do not show growth inhibition upon inhibitor treatment either in full serum or with addition of exogenous PDGF, suggesting that they may not utilize the PDGFR pathway for proliferation or survival under the conditions tested in vitro. However, when subjected to the diverse extracellular stimuli they will encounter in the in vivo environment, it seems likely that many tumor cells like these will respond to inhibition of the PDGFR pathway in such a setting.

FGFR Signaling in NSCLC

Figure 4:
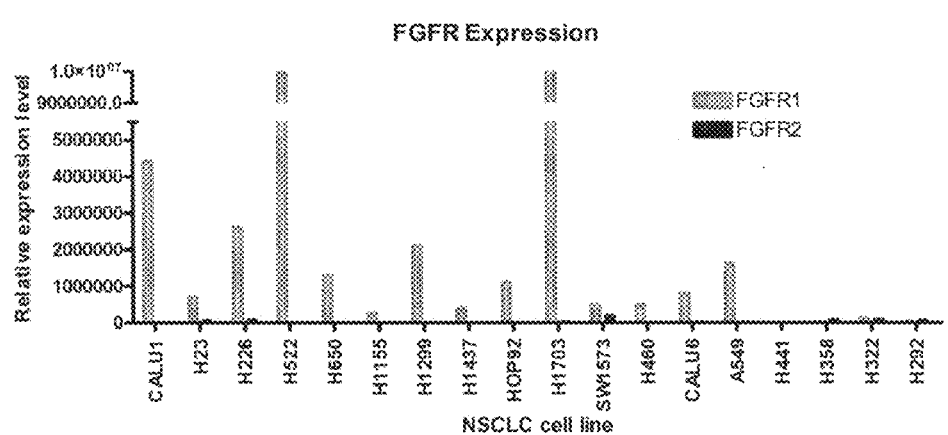
FIG. 4: Upregulation of FGFR Signaling Pathways in NSCLC. Total RNA was isolated from the indicated NSCLC cell lines. Expression levels of FGFR1 and FGFR2 were determined by RT-PCR. The data was corrected to GAPDH expression in each cell line and plotted as relative expression (arbitary units).

A quantitative PCR assay was carried out to analyze the expression levels of two members of the FGFR family (FGFR1 and FGFR2) in tumor cells (FIG. 4).

The results indicate that expression of the FGFR1 receptor is restricted to mesenchymal-like NSCLC cell lines, with no expression in the epithelial cell lines. H1703 and H522 express high levels of the FGFR1 receptor in relation to the other mesenchymal-like cell lines. The expression level of FGFR2 was low in all the cell lines tested irrespective of phenotype. These data suggest that FGFR1 is upregulated in mesenchymal-like NSCLC cell lines and may play a role in cell proliferation/survival signaling.

Figure 5:
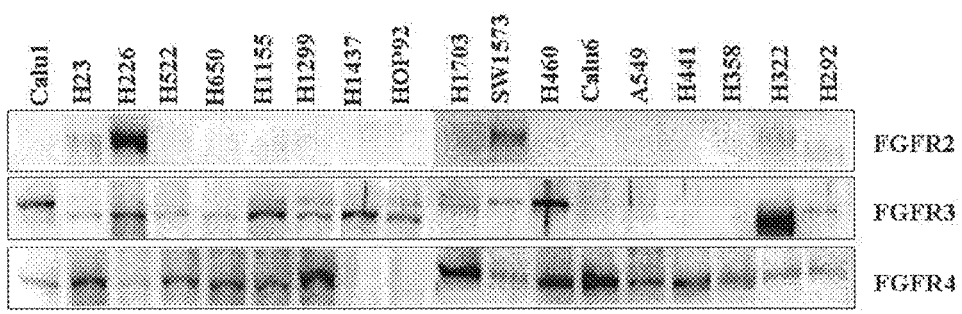
FIG. 5: FGFR Receptor Expression in NSCLC. Protein extracts were prepared from the indicated NSCLC cell lines. Lysates were separated by SDS-PAGE and transferred to nitrocellulose membrane. The membrane was probed with anti-FGFR2, anti-FGFR3 or anti-FGFR4 antibodies.

The protein levels of each of the four members of the FGF receptor family was analyzed by immunoblot analysis (FIG. 5). The results confirmed the RT-PCR analysis, suggesting that FGFR1 was expressed predominately in the mesenchymal-like cell lines, whereas FGFR2 was only expressed to any significant extent in SW1573 and H226 cells. Interestingly, H226, although expressing low levels of FGFR2 mRNA shows relatively high protein expression.

In addition it was also observed that FGFR3 is expressed primarily in the mesenchymal-like cells, except for H322, which shows high levels. FGFR4 is expressed to some degree in all of the cell lines analyzed.

Figure 6:
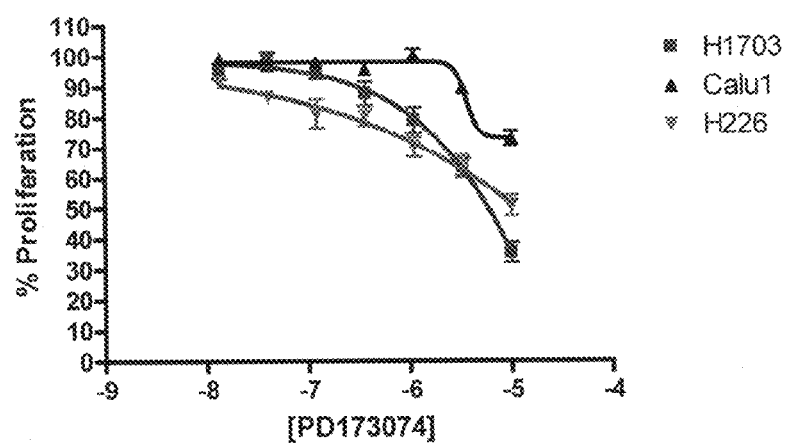
FIG. 6: Inhibition of FGFR activity in NSCLC. A. H1703 (■), Calu1 (▲) and H226 (▼) cells were treated with increasing concentrations of FGFR inhibitor (PD173074). After 72 hours incubation proliferation of the cells was measured by CellTitreGlo assay and plotted as a % proliferation relative to untreated cells.

To determine whether FGFR was involved in stimulating cell proliferation/survival signals in these cells a small molecule inhibitor PD173074 (Sigma-Aldrich, St. Louis, Mo.) which is specific for the FGFR family (specifically FGFR1 and FGFR3) was utilized. Two mesenchymal-like NSCLC cell lines, showing detectable levels of FGFR1, 3 and 4 were treated with increasing concentrations of PD173074 and cell proliferation assayed using the CELLTITERGLO™ cell viability assay (Promega, Madison Wis.) (FIG. 6). H1703 and H226 cells were growth inhibited by treatment with PD173074, whereas the inhibitor had little effect upon Calu1 cells.

In order to understand what impact the inhibitor had on intracellular signaling pathways in the two sensitive cell lines, the cells were treated with PD173074 in the presence or absence of exogenously added ligand. Activation of the ERK MAP kinase pathway was inhibited by PD173074 under both basal (FIG. 7, "Con") and ligand FIG. 7, "FGF") stimulated conditions. The AKT pathway was only inhibited after ligand stimulation in H1703 cells. Signaling in Calu1 cells was unaffected by PD173074.

Collectively these results indicate that mesenchymal-like cells have an increased level of FGF receptors, and at least two cell types, H1703 and H226, utilize signaling through the receptor to send cell survival and proliferation signals.

Figure 8:
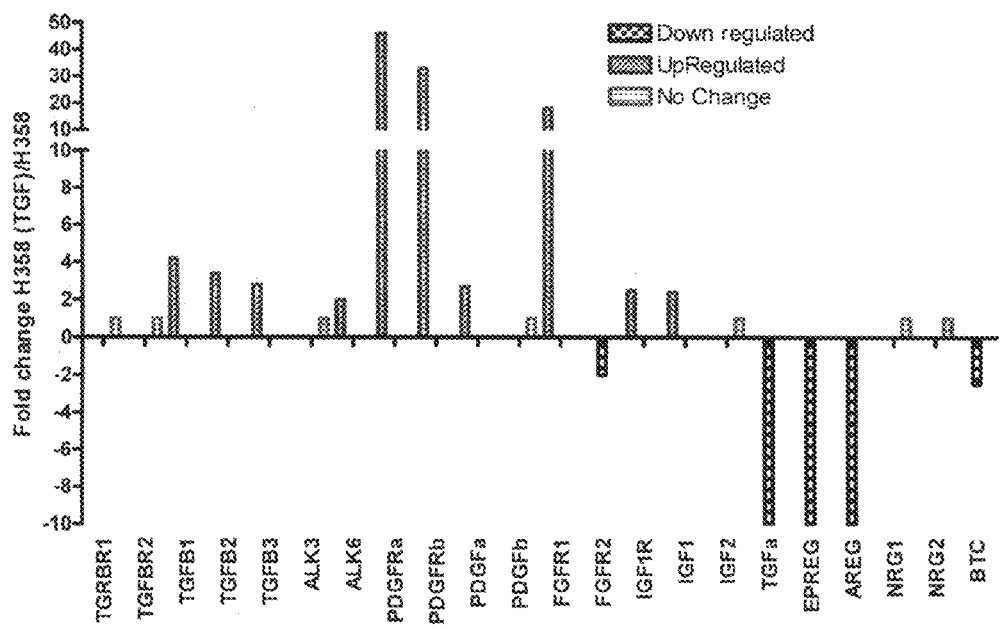
FIG. 8: Gene expression Changes in H358 cell treated with TGFβ. Total RNA was isolated for H358 and H358 cell treated with TGFβ3 (14 days). Expression of the indicated genes was analysed by RT-PCR and the data corrected to GAPDH expression in the respective cell line. Data is represented as fold-change in TGFβ-treated H358 cells as compared to untreated H358 cells.

PDGFR and FGFR upregulation can be observed as tumor cells are stimulated to undergo EMT, as for example in TGF-β3 treated H358 cells (FIG. 8).

Conclusions

In summary, the results described herein demonstrate that mesenchymal-like tumor cells that are relatively insensitive to EGFR kinase inhibitors, such as erlotinib, are "hybrid" tumor cells, in that they express characteristics of both epithelial and mesenchymal cells, and can be identified by determining the co-expression at similar levels of particular epithelial (e.g. cytokeratins, e.g. keratin 8 an/or keratin 18) and mesenchymal (e.g. vimentin) biomarkers. Thus, identification of such mesenchymal-like hybrid tumor cells is diagnostic of a tumor cell type that is relatively insensitive to inhibition by EGFR kinase inhibitors.

The results described herein also demonstrate that mesenchymal-like "hybrid" tumor cells have acquired elevated levels of other receptor kinases (e.g. PDGFR, FGFR) that can enhance the proliferation and mobility of the tumor cells. Thus, identification of such mesenchymal-like hybrid tumor cells is diagnostic of a tumor cell type that, while relatively insensitive to inhibition by EGFR kinase inhibitors, may be sensitive to inhibition by other receptor kinase inhibitors (e.g. inhibitors of FGFR or PDGFR). The data presented herein demonstrates that of the mesenchymal-like hybrid tumor cells examined 17% were inhibited by an inhibitor of either PDGFR or FGFR kinase, while 8% were inhibited by both. The percentage of hybrid tumor cells inhibited is likely to be considerably higher when other receptor kinases are considered, and/or when the growth of cells is monitored in an in vivo environment where ligand availability and sensitivity may be considerably enhanced.

Consequently, identification of a cancer patient's tumor cells as mesenchymal-like hybrid cells should provide physicians with a valuable diagnostic tool to help determine the potential mode of treatment of the patient, and thus enhance their chances of survival.

Abbreviations

EGF, epidermal growth factor; EMT, epithelial to mesenchymal transition; NSCLC, non-small cell lung carcinoma; HNSCC, head and neck squamous cell carcinoma; CRC, colorectal cancer; MBC, metastatic breast cancer; EGFR, epidermal growth factor receptor; PDGFR, platelet-derived growth factor receptor; FGFR, Fibroblast growth factor receptor; Brk, Breast tumor kinase (also known as protein tyrosine kinase 6 (PTK6)); IHC, immunohistochemistry; LC, liquid chromatography; MS, mass spectrometry; IGF-1, insulin-like growth factor-1; TGFα, transforming growth factor alpha; HB-EGF, heparin-binding epidermal growth factor; LPA, lysophosphatidic acid; TGFα, transforming growth factor alpha; $IC_{50}$, half maximal inhibitory concentration; pY, phosphotyrosine; wt, wild-type; PI3K, phosphatidyl inositol-3 kinase; GAPDH, Glyceraldehyde 3-phosphate dehydrogenase; TBS, tris-buffered saline.

Incorporation by reference

All patents, published patent applications and other references disclosed herein are hereby expressly incorporated herein by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for treating tumors or tumor metastases in a patient, comprising the steps of:
   (a) diagnosing the patient's likely responsiveness to EGFR, PDGFR and FGFR kinase inhibitors comprising:
      (i) measuring the combined expression levels of keratin 8 and 18 in tumor cells of a tumor sample;
      (ii) measuring the expression level of the mesenchymal biomarker vimentin in said tumor cells of the tumor sample; and
      (iii) diagnosing the patient as having low sensitivity to EGFR kinase inhibitors and potential high sensitivity to PDGFR or FGFR kinase inhibitors when vimentin is expressed, and is expressed at a similar level to the combined expression levels of said keratins in said tumor cells; and
   (b) administering to said patient a therapeutically effective amount of a PDGFR or FGFR kinase inhibitor when low sensitivity to inhibition by EGFR kinase inhibitors and potential high sensitivity to PDGFR or FGFR kinase inhibitors is diagnosed for said patient.

2. The method of claim 1, wherein the EGFR kinase inhibitor comprises erlotinib.

3. The method of claim 1, wherein the PDGFR kinase inhibitor comprises imatinib, sunitib malate, dasatinib, sorafenib, axitinib, RPR127963, CP-868596, tandutinib, motesanib, leflunomide, OSI-930, XL-999, SU6668, CHIR-258, RO4383596, or BIBF-1120.

4. The method of claim 1, wherein the FGFR kinase inhibitor comprises RO-4396686, CHIR-258, PD 173074, PD 166866, ENK-834, ENK-835, SU5402, XL-999, SU6668, CHIR-258, RO4383596, or BIBF-1120.

5. The method of claim 1, wherein one or more additional anti-cancer agents or treatments are co-administered simultaneously or sequentially with the EGFR, PDGFR or FGFR kinase inhibitor.

6. The method of claim 5, wherein the additional anti-cancer agent comprises an EGFR, PDGFR or FGFR kinase inhibitor.

7. The method of claim 6, wherein the EGFR kinase inhibitor comprises erlotinib.

8. The method of claim 1, wherein keratin 8 and keratin 18 expression are determined using a pan-specific antibody that binds to keratin 8 and keratin 18.

9. A method for treating tumors or tumor metastases in a patient, comprising administering to said patient a therapeutically effective amount of a PDGFR or FGFR kinase inhibitor when low sensitivity to inhibition by EGFR kinase inhibitors and potential high sensitivity to PDGFR or FGFR kinase inhibitors is diagnosed for said patient by the steps of (i) measuring the combined expression levels of keratin 8 and 18 in tumor cells of a tumor sample; (ii) measuring the expression level of the mesenchymal biomarker vimentin in said tumor cells of the tumor sample; and
   (iii) diagnosing the patient as having low sensitivity to EGFR kinase inhibitors and potential high sensitivity to PDGFR or FGFR kinase inhibitors when vimentin is expressed, and is expressed at a similar level to the combined expression levels of said keratins in said tumor cells.

* * * * *